(12) United States Patent
Dhaniyala et al.

(10) Patent No.: US 8,919,183 B1
(45) Date of Patent: Dec. 30, 2014

(54) HIGH-FLOW DUAL-CHANNEL DIFFERENTIAL MOBILITY ANALYZER

(75) Inventors: Suresh Dhaniyala, Potsdam, NY (US); Praney Dubey, Karnatka (IN)

(73) Assignee: Clarkson University, Potsoam, NY (US)

( * ) Notice: Subject to any disclaimer, the term of this patent is extended or adjusted under 35 U.S.C. 154(b) by 366 days.

(21) Appl. No.: 12/590,063

(22) Filed: Nov. 2, 2009

Related U.S. Application Data

(60) Provisional application No. 61/193,144, filed on Oct. 31, 2008.

(51) Int. Cl.
*G01N 1/26* (2006.01)
(52) U.S. Cl.
USPC ............... 73/28.04; 73/28.02; 73/865.5

(58) Field of Classification Search
USPC .................. 73/865.5, 28.02, 28.04
See application file for complete search history.

(56) References Cited

U.S. PATENT DOCUMENTS

2006/0266132 A1* 11/2006 Cheng et al. ............... 73/865.5

* cited by examiner

*Primary Examiner* — Paul West
(74) *Attorney, Agent, or Firm* — Gerow D. Brill

(57) ABSTRACT

A new instrument for electrical-mobility based size segregation of particles at high resolution is described. The instrument called the high-flow dual-channel differential mobility analyzer (HD-DMA) comprises of five flows: a polydisperse aerosol flow, a clean sheath flow, two monodisperse sample flows and a residual excess flow. High resolution measurements are possible because of the large sheath flowrates that are permissible in this instrument.

13 Claims, 27 Drawing Sheets

HIGH-FLOW DUAL-CHANNEL DIFFERENTIAL MOBILITY ANALYZER

CROSS REFERENCE

This application is related Provisional Patent Application Ser. No. 61/193,144 filed on 31 Oct. 2008 and is hereby incorporated herein in full.

GOVERNMENT RIGHTS

Support for the research disclosed was from the National Science Foundation under Grant Number ATM 0548036.

FIELD OF THE INVENTION

This application is related to instrumentation and apparatus for size and segregation of particles. In particular, the instrumentation and apparatus is aimed at segregating sub-micron sized particles.

BACKGROUND OF THE INVENTION

DMA: Background Information

The revolution in the field of sub-micron particle sizing came with the development of the differential mobility analyzer (DMA) and the theoretical description of its working by Liu, N. Y. H., and Pui, D. Y. H. (1974). A submicron Aerosol Standard and the Primary, Absolute Calibration of the Condensation Nuclei Counter, J. Colloid and interface Sci. 47:155-171 and by Knutson, E. O., and Whitby, K. T. (1975). Aerosol classification by Electrical Mobility: apparatus theory and applications. J. Aerosol Sci. 6:443-451, both hereby incorporated herein by reference. The DMA uses a combination of applied electric and flow fields to classify particles by their electrical mobility and sampling from a port at an appropriate location can result in an output of particles with a narrow range of electrical mobilities. While the initial application of DMAs was primarily for generation of monodisperse particles, the development of the condensation particle counter (CPC) (See Agarwal, J. K. and Sem, G. J. (1980) Continuous flow, single-particle-counting condensation nucleus counter, J. Aerosol Sci. 11:343-357 hereby incorporated herein by reference.) enabled its deployment for particle size distribution measurements. Initial size distribution measurements with the DMA were made with a stepping-mode operation, where the voltages were sequentially stepped to output particles of different mobilities. This technique, called the differential mobility particle sizer (DMPS), required significant "dead-time" between measurements to ensure steady state aerosol sampling. Accurate measurements with the DMPS required ~20 minutes to cover a broad range of mobilities.

Wang and Flagan (See Wang, S. C., and Flagan, R. C. (1990) Scanning Electrical Mobility Spectrometer, Aerosol Sci. Technol. 13: 230-240 hereby incorporated herein by reference) showed that an exponential voltage ramp can be used to speed up measurements, and for this operation the shape of transfer function remains unchanged throughout the scan. This instrument, known as Scanning Electrical Mobility Analyzer (SEMS), decreased measurement time to ~5 minutes. Faster measurements with SEMS are complicated by the effect of particle concentration smearing in the CPC and plumbing delays between the DMA and the CPC. There have been several approaches to account for these non-idealities. The effect of smearing and plumbing delay on transfer function was considered in Russell et al. (See Russell, L. M., Flagan, R. C., and Seinfeld, J. H. (1995). Asymmetric Instrument Response Resulting from Mixing Effects in Accelerated DMA-CPC Measurements, Aerosol Sci. Technol. 23:491-509. hereby incorporated by reference.) In that work, plumbing delay was accounted for by considering the transit time between DMA exit and detector, and smearing was modeled as a Continuously Stirred Tank Reactor (CSTR). A more accurate, but complicated, transfer function was obtained by combining these effects with the classical transfer function. A simpler method to account for the effect of smearing was introduced by Collins et al (See Collins, D. R., Flagan, R. C., and Seinfeld, J. H. (2002) Improved Inversion of Scanning DMA Data, Aerosol Science and technology. 36:1-9 hereby incorporated by reference herein.). In their work, transfer function determination and smearing effect were treated separately, reducing the complexity of calculations and data analysis. In both these approaches the transfer function of the scanning DMAs were assumed to be the same as that derived by Knutson and Whitby (1975) for fixed voltage DMAs.

Recently, Collins et al (See Collins, D. R., Cocker, D. R., Flagan, R. C., and Seinfeld, J. H. (2004) The Scanning DMA Transfer Function, Aerosol Science and technology. 38:833-850 hereby incorporated herein by reference.) analyzed the scanning mode DMA transfer functions obtained using simulations based on the approach of Hagwood et al. (See Hagwood, C., Sivathanu, Y., and Mulholland, G. (1999). The DMA Transfer Function with Brownian Motion a Trajectory/Monte-Carlo Approach, Aerosol Sci. Technol. 30:40-61 hereby incorporated herein by reference.) for scan times ranging from 20 to 3600 s for non-diffusive particles. For small scan times, relative to the particle residence times in the classification region, the transfer functions for scanning DMAs were shown to be substantially different from the expected triangular transfer function. Their calculation technique, using Monte-Carlo simulations, is time consuming and not amenable for real-time transfer function calculation. The recent applications of fast scan SEMS operation (e.g., Han et al., (See Han, H. S., Chen, D. R., Pui, D. Y. H., and Anderson, B. E. (2000). A Nanometer Aerosol Size Analyzer (ASA) for Rapid Measurement of High-Concentration Size Distributions, J. Nanoparticle Research 2:43-52 hereby incorporated herein by reference.) and Shah and Cocker (See Shah, S. D. and Cocker, D. R. (2005). A Fast Scanning Mobility Particle Spectrometer for Monitoring Transient Particle Size Distributions, Aero. Sci. Technol. 39:519-526 hereby incorporated herein by reference) suggests a need for near real-time transfer function calculation, accounting for the scan time of SEMS operation.

A semi-theoretical approach is introduced for near real-time transfer function calculation of scanning DMAs. Considering a cylindrical geometry and upscan operation, time-dependent particle trajectory equation is obtained and solved numerically to obtain the time-evolution of sampled concentration for a selected mobility. A simple procedure is outlined to then convert the time-spectrum of particles of one mobility to a mobility-based transfer function. The calculations suggest that fast scanning can significantly smear the transfer functions and also shift the mean mobility for a selected voltage.

A DMA consists of a coaxial cylinder with four flows, of which two flows—sheath and aerosol—are introduced at the top, and two flows—sample and excess flow—exit from bottom. An electric field of known strength is applied in the radial direction across the classification region. Charged particles coming with the aerosol flow traverse the radial direction under the influence of electric field. For a constant axial flow field, particles of different diameters (or electrical mobility)

travel different distances in the classification region. High mobility particles are collected on the inner cylinder wall while low mobility particles exit with the excess flow. Particles of a narrow range of mobility are collected through the sample flow. The particles coming out of sample flow are counted using a particle counter obtaining concentrations of the classified particles. Initial size distribution measurements with the prior art DMAs were made with a stepping-mode operation, where the voltages were sequentially stepped to output particles of different mobilities. This technique, called the differential mobility particle sizing (DMPS), requires significant "dead-time" between measurements to ensure steady state aerosol sampling, and hence, accurate size distribution measurement with the DMPS requires approximately 20 minutes.

A narrow, but finite, range of mobilities exit the DMA for a selected voltage. This distribution of sampled mobilities for selected operating conditions is the instrument transfer function. For non-diffusive particles and balanced flow operation (i.e., aerosol flow equal to sample flow), the range of mobilities sampled from the DMA depends on the ratio of sample and sheath flows (Knutson and Whitby, 1975. Similar results were obtained by Stolzenburg (See Stolzenburg, M. R. (1988). An Ultrafine Aerosol Size Distribution Measuring System, Ph.D. Thesis, University of Minnesota, Minneapolis, hereby incorporated herein by reference.) following a slightly different approach. Here, we present results that are partly taken from both papers.

Following the approach of Knutson and Whitby (1975), we neglect particle inertia and diffusion and assume that the flow field is axisymmetric, laminar, and incompressible. Then the governing equations for radial and axial particle motion are:

$$\frac{dr}{dt} = u_r + ZpE_r \quad [1.2]$$

$$\frac{dz}{dt} = u_z + ZpE_z$$

where, r is the radial distance traveled by the particle, z is the axial distance traveled by the particle, $u_r$ is the radial velocity of the particle, $u_z$ is the axial velocity of the particle, Zp is the particle mobility, $E_r$ is the electric field component in the radial direction and $E_z$ is the electric field component in the axial direction.

The expression for stream function ψ and electric flux function φ can be written as $$\Psi(r, z) = \int^{r,z} [ru_r dz - ru_z dr] \quad [1.3]$$

$$\varphi(r, z) = \int^{r,z} [rE_r dz - rE_z dr]$$

Using these expressions, the substantial time derivative of ΨZpψ can be obtained as $$\frac{d}{dt}(\psi + Zp\varphi) = \frac{\partial}{\partial t}(\psi + Zp\varphi) + \frac{dr}{dt}\frac{\partial}{\partial r}(\psi + Zp\varphi) + \frac{dz}{dt}\frac{\partial}{\partial z}(\psi + Zp\varphi) \quad [1.4]$$

$$\frac{d}{dt}(\psi + Zp\varphi) = 0 + \frac{dr}{dt}(-ru_z - ZprE_z) + \frac{dz}{dt}(ru_r + ZprE_r)$$

-continued $$\frac{d}{dt}(\psi + Zp\varphi) = 0 + \frac{dr}{dt}\left(-r\frac{dz}{dt}\right) + \frac{dz}{dt}\left(r\frac{dr}{dt}\right) = 0$$

This derivation implies that the particles travel along trajectories in such a way that (ψ+Zpφ) remains constant. For particles of a selected mobility, the difference between two points along a trajectory implies that Δψ+ZpΔφ=0. Thus for a non-diffusive particle, the probability density function of the transfer function ($f_{trans}$) can be written as:

$$f_{trans}(\psi_{out}, \psi_{in}) = \delta(\psi_{out} - \psi_{in} + Zp\Delta\varphi) \quad [1.5]$$

where δ is dirac delta function. If we define $\psi_1$ and $\psi_2$ as stream functions at the outer and inner radii of aerosol inlet and $\psi_3$ and $\psi_4$ as stream function at the outer and inner radii of sample exit, then the expression for DMA transfer function (Ω) is:

$$\Omega = \int_{\psi_1}^{\psi_2} \left( \int_{\psi_3}^{\psi_4} f_{trans}(\psi_{out}, \psi_{in}) d\psi_{out} \right) f_{in}(\psi_{in}) d\psi_{in} \quad [1.6]$$

where the inlet probability density function can be written as $$f_{in} = \frac{1}{\psi_2 - \psi_1} \quad [1.7]$$

For non-diffusive particles, the transfer function expression is:

$$\Omega = \frac{1}{2}\frac{1}{\psi_2 - \psi_1}(-|\psi_4 - \psi_2 + Zp\Delta\varphi| + \quad [1.8]$$

$$|\psi_4 - \psi_1 + Zp\Delta\varphi| + |\psi_3 - \psi_2 + Zp\Delta\varphi| - |\psi_3 - \psi_1 + Zp\Delta\varphi|)$$

The stream functions are related to the volumetric flow, which are expressed as:

$$2\pi(\psi_2 - \psi_1) = q_a \text{(aerosol)}$$

$$2\pi(\psi_4 - \psi_2) = q_{sh} \text{(sheath)}$$

$$2\pi(\psi_4 - \psi_3) = q_s \text{(sample)}$$

$$2\pi(\psi_3 - \psi_1) = q_e \text{(excess)} \quad [1.9]$$

Expressing the transfer function in the form of flow rates rather than stream function, the transfer function can be expressed as:

$$\Omega = \frac{1}{q_a}\max\left(0, \min\left(q_a, q_s, \left(\frac{1}{2}(q_a + q_s) - \left|2\pi Zp\Delta\varphi + \frac{1}{2}(q_e + q_{sh})\right|\right)\right)\right) \quad [1.10]$$

This expression can be further simplified in the form of dimensionless mobility and flow parameters. The dimensionless mobility is defined as:

$$\overline{Zp} = \frac{Zp}{Zp^*} = \frac{4\pi LVZp}{(Q_{sh} + Q_e)}\log\frac{r_2}{r_1} \quad [1.11]$$

where $r_2$ is the radii of outer cylinder, $r_1$ is the radii of the inner cylinder, L is the length of the classification region, V is the voltage applied across classification region. The dimensionless flow parameters are:

$$\beta = \frac{q_s + q_a}{q_{sh} + q_e} \quad \delta = \frac{q_s - q_a}{q_s + q_a} \quad [1.12]$$

Then the transfer function be written as:

$$\Omega = \frac{1}{2\beta(1-\delta)} \quad [1.13]$$
$$(|\overline{Zp} - (1-\beta)| + |\overline{Zp} - (1+\beta)| - |\overline{Zp} - (1-\beta\delta)| - |\overline{Zp} - (1+\beta\delta)|)$$

FIG. 1 illustrates the classical DMA transfer function (Knutson and Whitby, 1975). Stolzenburg (1988) further extended the work of Knutson and Whitby by incorporating the effect of diffusion on transfer function. Hagwood et al. (1999) who used Monte Carlo approach to obtain the transfer function validated the diffusive transfer functions of Stolzenburg. In this approach, the effect of wall loss and axial diffusion in the classification region was considered. It was observed that wall loss was significant for very small particles, as their diffusion coefficient were relatively high. Also, the wall loss was seen to be much higher for plug flow than for the parabolic flow profile.

The operational regime where diffusion becomes significantly more important is estimated on the basis on resolution analysis. The DMA resolution is expressed as the ratio of mobility at the peak of the transfer function to the full width of the transfer function at the half the maximum height (Zhang and Flagan, 1996). For non-diffusive transfer function, resolution can be written as $$R = \frac{Zp^*}{\Delta Zp_{fwhm}} = \frac{1}{\beta(1+|\delta|)} \quad [1.14]$$

For the diffusive transfer function, resolution does not have a closed form description but can be estimated from transfer functions. Flagan (1999) showed that for balanced flow, the DMA resolution is a function of the potential difference across the classification region. For typical DMA operation, it was observed that diffusion was significant for voltages <~100 volt.

Scanning DMA:
Operating the DMA with a fixed voltage will result in the output of particles with a narrow range of mobilities, and the transfer function for this operation can be determined using the approach of Knutson and Whitby (1975), Stolzenburg (1988), and others. Stepping the operating voltages will result in size distribution measurement in 10 minutes to one hour, depending on the number of size bins and particle residence time in the DMA and the counter. Often, high temporal resolution of concentration measurements is required, for e.g., for aircraft-based measurements, smog chamber experiments, combustion processes etc. For those situations, fast operation of DMA is inevitable. For such applications, Wang and Flagan (1990) proposed to operate the DMA with a continuous variation of the electric field in the classification region. For fixed voltage operation they explained that the set of particles travelling from the aerosol inlet to the sample exit travels the same trajectory across the classification region, independent of the voltage value. Wang and Flagan (1990) showed that this behavior is preserved only for exponential variation in voltage among all possibilities of continuous variation of voltage. They also showed that this behavior is important for keeping the shape of non-diffusive transfer function independent of peak mobility ($Zp^*$) This important observation by Wang and Flagan (1990) lead to the scanning operation of the DMA, and the resultant instrument was referred to as the scanning electrical mobility spectrometer (SEMS). This instrument was commercialized by TSI and named as scanning mobility particle spectrometer (SMPS). In scanning operation, the voltage is either increased or decreased exponentially. The expressions for voltage scan are:

$$V_{up}(t) = V_{min} e^{\frac{t}{\tau}} \quad [1.15]$$
$$V_{down}(t) = V_{max} e^{\frac{t}{\tau}}$$
$$\tau = \frac{scantime}{\log\left(\frac{V_{max}}{V_{min}}\right)}$$

Where $V_{up}$ is the voltage variation with time during up scan and $V_{down}$ is the voltage variation with the time during down scan, $V_{min}$ is the minimum voltage applied across the classification region in a single scan time and $V_{max}$ is the maximum voltage applied across the classification region in a single scan time.

The scan time shown in the expression is the duration over which the voltage is changed. Using this approach the measurement time is decreased significantly to less than 5 minutes. Faster measurements with SEMS become complicated by the effect of particle concentration smearing in the counter and plumbing delays between the DMA and the counter. There have been several approaches to account for these non-idealities. The effect of smearing and plumbing delay on transfer function was considered in Russell et al. (1995). In that work, plumbing delay was accounted for by considering the transit time between DMA exit and detector, and smearing was modeled as a Continuously Stirred Tank Reactor (CSTR). A more accurate, but complicated, transfer function was obtained by combining these effects with the classical transfer function. A simpler method to account for the effect of smearing was introduced by Collins et al (2002). In their work, the transfer function determination and the smearing effect were treated separately, reducing the complexity of calculations and data analysis. In both these approaches the transfer function of the scanning DMAs were assumed to be the same as that derived by Knutson and Whitby (1975) for fixed voltage DMAs.

Recently, Collins et al (2004) analyzed the scanning mode DMA transfer functions obtained using simulations based on the approach of Hagwood et al (1999) for scan times ranging from 20 to 3600 s for non-diffusive particles. For small scan times, relative to the particle residence times in the classification region, the transfer functions for scanning DMAs were shown to be substantially different from the expected triangular transfer function. Their calculation technique using Monte-Carlo simulations, is time consuming and not amenable for real-time transfer function calculation.

In the Monte Carlo simulations done by Collins et al (2004), particles were injected from 50 different injection locations in aerosol inlet at every 5 millisecond. Particle paths were obtained by solving the trajectory equations. Particles were "collected" at 2 second time intervals at the sample exit for transfer function estimation. These simulations were done for 1000 different mobilities and transfer functions were obtained for up- and down-scan operation. The central mobility location ($Z_p^*$) obtained using their Monte Carlo simulations were seen to be different from that obtained from classical relations. The other important observation from their work was that particle trajectory between the aerosol inlet and sample exit varied as a function of $t_r/t$. Thus, it was concluded that the variation in the transfer function is related to $t_r/t$.

The recent applications of fast scan SEMS operation (e.g., Han et al., 2000; Shah and Cocker 2005) suggests a need for near real-time transfer function calculation, accounting for the scan time of SEMS operation. A semi-theoretical approach is introduced for near real-time transfer function calculation of scanning DMAs. Considering a cylindrical geometry and upscan operation, time-dependent particle trajectory equation is obtained and solved numerically to obtain the time-evolution of sampled concentration for a selected mobility. A simple procedure is outlined to convert the time-spectrum of particles of one mobility to a mobility-based transfer function. The calculations suggest that fast scanning can significantly smear the transfer functions and also shift the mean mobility for a selected voltage.

DMA Background and Operation:

A differential mobility analyzer (DMA) can classify particles based on electrical mobility and output particles over a narrow range of electrical mobilities. It is a standard instrument for sizing sub-micron aerosol and is commonly used in conjunction with aerosol generators to obtain monodisperse particles. DMAs typically have a cylindrical geometry, with an inner rod maintained at a selected HV and the outer cylinder at ground potential. Polydisperse aerosol is introduced near the outer cylinder and clean sheath flow is sent through the DMA between the aerosol flow and the inner rod. Charged particles will migrate across the sheath gas and be collected at distances determined by their electrical mobility. Particles of just the right size will be sampled through the sample port near the end of the central rod. The rest of the flow is pumped out as excess flow. For fast size distribution measurements over a broad particle size range, a new DMA design is being introduced here.

SUMMARY OF THE INVENTION

Figure 1A:
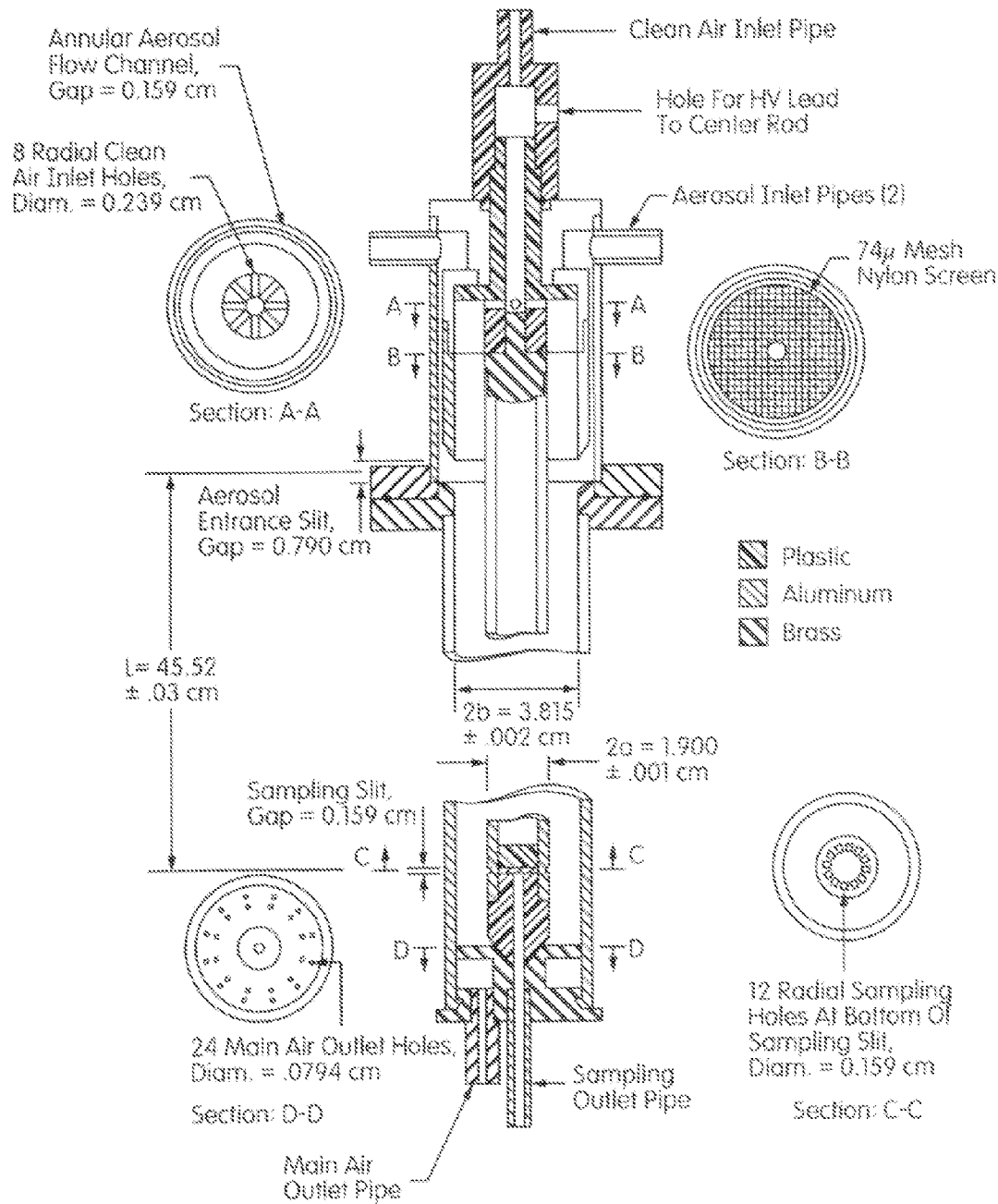
FIG. 1 illustrates the classical DMA transfer function from Knutson and Whitby, 1975.
Figure 1B:
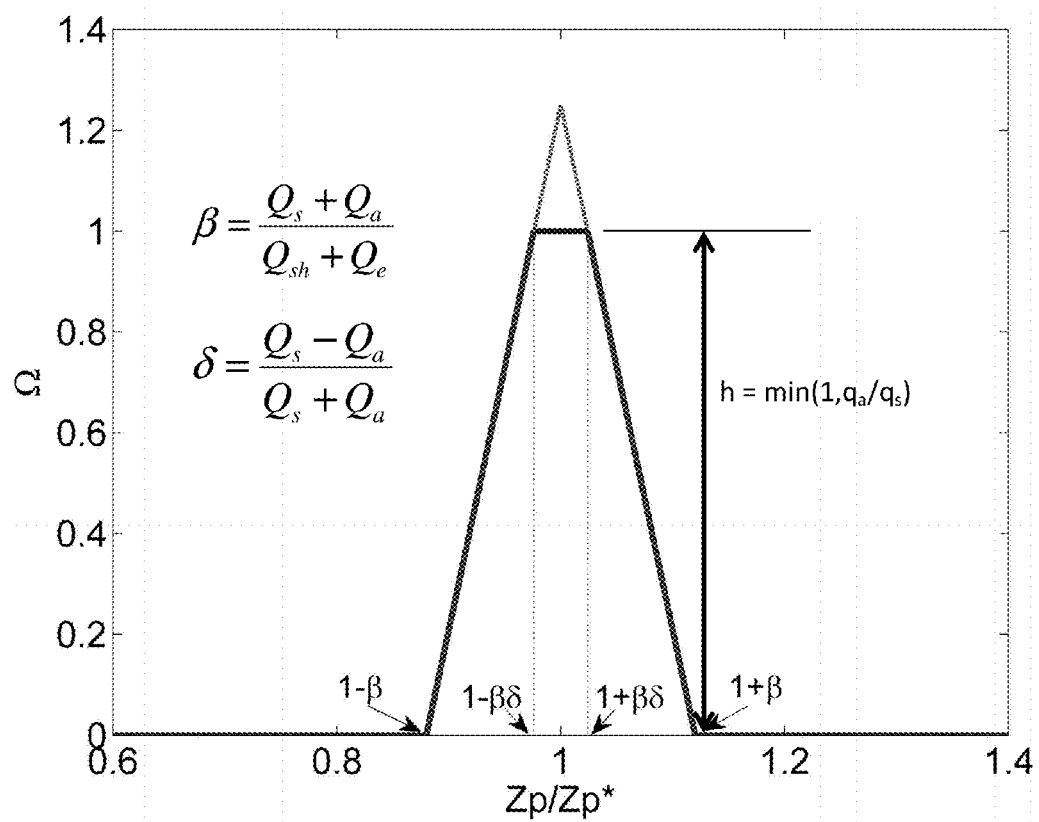

The present invention is directed to a method, apparatus and instrumentation that satisfies a need for there is a need for a method, apparatus and instrumentation for obtaining fast size distribution measurements over a broad particle size range as described below. A new instrument for electrical-mobility based size segregation of particles with high resolution is described here. The instrument called the high-flow dual-channel differential mobility analyzer (HD-DMA) comprises of five flows: a polydisperse aerosol flow, a clean sheath flow, two monodisperse sample flows and a residual excess flow. The polydisperse aerosol flow can be in the range of 0.3-30 LPM. The flowrate range of the two monodisperse sample flows is the same as that of the polydisperse flow. The sheath flow range is 10-300 LPM and is generally chosen to be a magnitude higher (ten times) than the polydisperse aerosol flow. The sheath and polydisperse flows are introduced near the outside radii of a cylindrical annular classification region through hemispherical entrance regions. This design ensures laminar, uniformly-distributed flows entering the classification region, without any "dead-volumes". Particles are mobility-segregated in the classification region and the classified particles are sampled at two locations in the classification region. One of the locations is close to the entrance (classification length of 5 cm) from where high mobility particles are sampled. The other location is towards the end of the classification region (classification length 22.5 cm) from where lower-mobility particles are sampled. All flows are maintained laminar in their channels, to avoid instrument performance degradation due to turbulence. The sampled "monodisperse" particles can be collected for off-line analysis or counted with a condensation particle counter (CPC) or an electrometer for size distribution measurement. The large sample flows ensures sufficient counts in ~1 sec/channel even under typical atmospheric conditions (<100 cm$^{-3}$), thus permitting fast scan measurements from aircrafts. High resolution measurements are possible because of the large sheath flowrates that are permissible in this instrument.

The HD-DMA disclosed herein includes several novel features. Firstly, the use of large dimensions for the classification region enables a high-flowrate (up to 200 LPM) operation while keeping the flows laminar. Secondly the HD-DMA uses hemi-spherical entrance sections to provide symmetrical aerosol and sheath flows. The HD-DMA utilizes a low pressure drop design that permits the use of a low-power recirculating blower to recirculate the excess and sheath flows. The use of multiple aerosol sample channels ensures fast measurement and increases the range of particle sizes than can be classified and measured with the DMA.

"Monodisperse" sample ports are designed to ensure fast size distribution measurement. For this, parabolic curved channels are used to transport the particles sampled from the classification region to the exit sample port and this design results in minimal mixing regions where particles can possibly collect and cause a "smear" effect (i.e., emerge at other times and thus, distort the sampled size distributions).

Combined with the fast-scan transfer function calculation approach of discussed below and from an article by the inventors (Dubey and Dhaniyala (2008)), the HD-DMA instrument can make size distribution measurements in less than 20 seconds even under conditions of low total number concentrations (~100 cm$^{-3}$) over a broad size range.

The use of a high sheath flow and the presence of multiple sample ports enable the HD-DMA to classify particles over a size range of 1.6 nm to 700 nm—a size range broader than any DMA currently known to the applicants.

The HD-DMA disclosed herein is a differential mobility analyzer for aerosol measurements, including a plurality of hemispheric entrance regions including at least one inlet for receiving an aerosol, the aerosol including a plurality of charged particles for analysis; a second at least one inlet separate from but concentric with the first input for receiving a sheath flow; a classifying region receiving the aerosol and sheath flow, the classification region having an inner and outer radii and a plurality of parabolic shaped concentric output ports located in serially lower positions within the classification region; a source of voltage coupled to said inner and outer radius for creating an electric field within said classification region, wherein said analyzer has a low Reynolds number, and hence laminar flow in the classification region, while maintaining a moderately high sheath flow (up to ~300 liters per minute) by using large radii for the inner and outer cylinders. A location of last of the plurality of the output ports in the classification region closer to the entrance flow, but beyond the streamlines of the aerosol entrance flow, permits sample particles as large as 2.5

The disclosure discusses a method for measuring a size distribution of aerosols, including the steps of: providing a differential mobility analyzer; providing an aerosol including a plurality of charged particles for analysis; injecting the aerosol into a classification region via a plurality of hemispheric entrance regions including at least one inlet for receiving the aerosol and further providing a second at least one inlet separate from but concentric with the first input for receiving a sheath flow; coupling a voltage to an inner and outer radii of the classification region creating an electric field there between; providing a plurality of parabolic shaped concentric output ports located at a plurality of serially lower positions within the classification region withdrawing a sampling flow using the concentric output ports at least two of the plurality of positions, wherein different mean particle sizes are withdrawn.

DESCRIPTION OF THE INVENTION

Primary Features of HD-DMA

The applicants have named the instrumentation and method of using the differential mobility analyzer disclosed as an HD-DMA due to its ability to select narrow ranges of sub-micron sized particles As will be discussed in more detail below, the HD-DMA disclosed herein includes several novel features. Firstly, the use of large dimensions for the classification region enables a high-flowrate (up to 200 LPM) operation while keeping the flows laminar. Secondly the HD-DMA uses hemi-spherical entrance sections to provide symmetrical aerosol and sheath flows. The HD-DMA utilizes a low pressure drop design that permits the use a low-power recirculating blower to recirculate the excess and sheath flows. The use of two aerosol sample channels ensures fast measurement and increases the range of particle sizes than can be classified and measured with the DMA.

"Monodisperse" sample ports are designed to ensure fast size distribution measurement. For this, parabolic curved channels are used to transport the particles sampled from the classification region to the exit sample port and this design results in minimal mixing regions where particles can possibly collect and cause a "smear" effect (i.e., emerge at other times and thus, distort the sampled size distributions).

Combined with the fast-scan transfer function calculation approach of discussed below and from an article by the inventors (Dubey and Dhaniyala (2008)), the HD-DMA instrument can make size distribution measurements in less than 20 seconds even under conditions of low total number concentrations (~100 cm$^{-3}$) over a broad size range.

The use of a high sheath flow and the presence of multiple sample ports enable the HD-DMA to classify particles over a size range of 1.6 nm to 700 nm—a size range broader than any DMA currently known to the applicants.

The first major portion of this disclosure will describe a two-step approach for a fast-scan transfer function based upon the article by the applicants. This will be followed by a description of the HD-DMA apparatus.

Fast-Scan Transfer Function Theory

Figure 2:
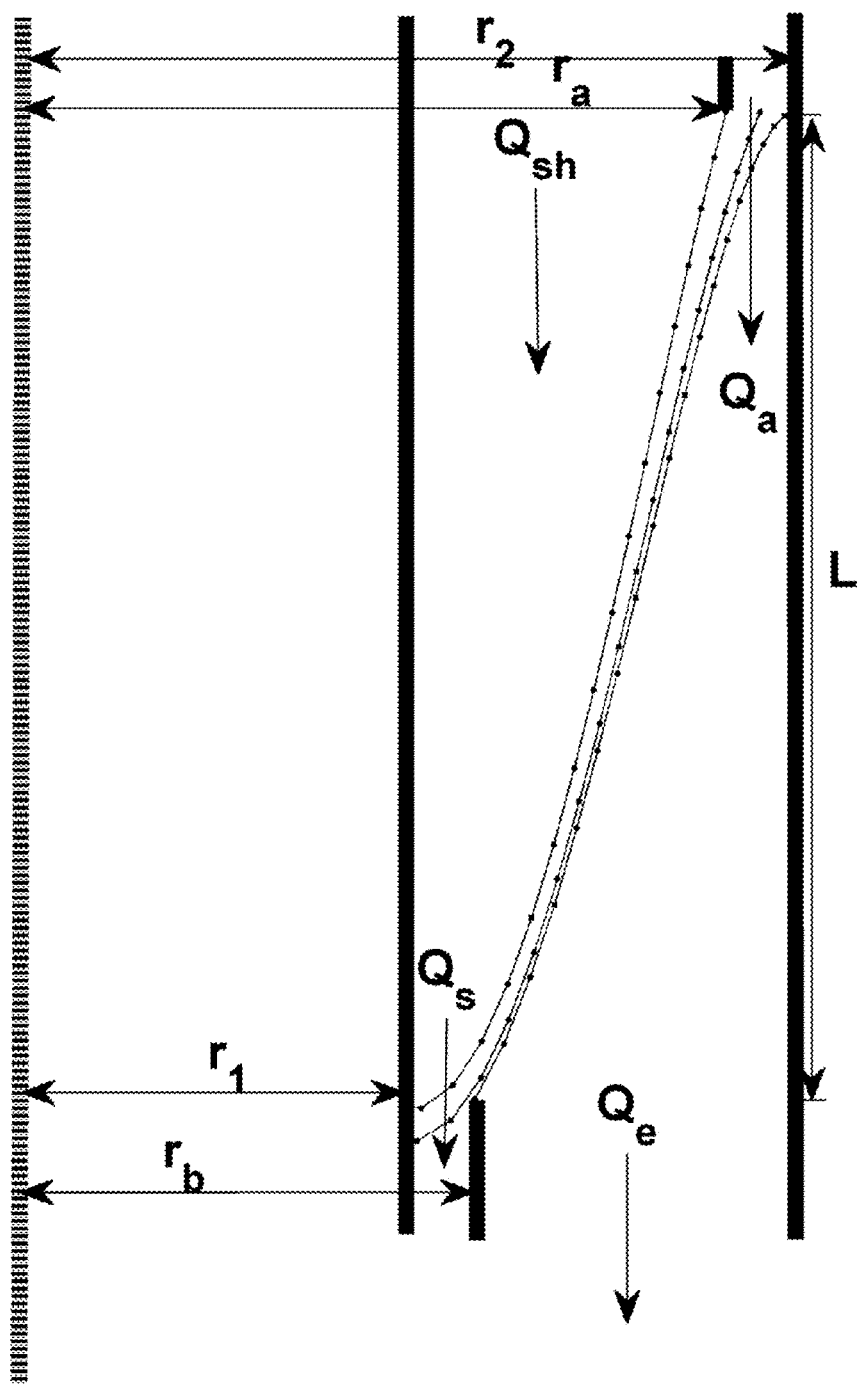
FIG. 2 illustrates a schematic diagram illustrating the simplified 2-D axi-symmetric geometry of the classification region; used in this study.

To determine the transfer function of a scanning DMA, a two-step approach is used: first, the trajectory equation is solved to find the position of particles at different times in the classification region and second, the transfer function is determined by the solution of the trajectory equation for a large number of particles injected at different locations in the aerosol inlet over a range of injection times. For particle trajectory calculations, it is assumed that the flow in the classification region is fully developed and the electric field in this region is temporally and spatially uniform, i.e., non-uniformities associated with the inlet and exit of the classification region are not considered. FIG. 2 illustrates the simplified 2-D axi-symmetric geometry of the classification region used in this study.

For the simplified classification region geometry (FIG. 2) operating under the above assumptions, the radial equation of particle trajectory at any time t is:

$$\frac{dr}{dt} = -\frac{Z_p V}{r \ln\left(\frac{r_2}{r_1}\right)} = -\frac{Z_p V_0 e^{\left(\frac{t}{\tau}\right)}}{r \ln\left(\frac{r_2}{r_1}\right)}, \quad [1]$$

where $Z_p$ is the particle mobility, V is the instantaneous voltage, $V_0$ is the voltage applied to the central rod at the beginning of scan, $\tau$ is the scanning time constant, given by $$\tau = \frac{t^s}{\ln\left(\frac{V_{max}}{V_0}\right)}, \quad [2]$$

where $t^s$ is the scan time and $V_{max}$ is the maximum voltage applied at the end of the upscan operation. Axial displacement of particles is determined from the solution of:

$$\frac{dz}{dt} = Ar^2 + B\ln(r) + C, \quad [3]$$

where the constants A, B, C are:

$$A = \frac{1}{4\mu}\frac{dp}{dz}, \quad [4]$$

$$B = -\frac{1}{4\mu}\frac{dp}{dz}\frac{r_2^2 - r_1^2}{\ln\left(\frac{r_2}{r_1}\right)}, \quad [5]$$

$$C = \frac{1}{4\mu}\frac{dp}{dz}\left(\frac{r_2^2 - r_1^2}{\ln\left(\frac{r_2}{r_1}\right)}\ln(r_1) - r_1^2\right), \quad [6]$$

where $\mu$ is the viscosity of the air and dp/dz is the constant pressure gradient for flow in the annular region. If a particle is injected at an initial radial location, $r_i$, then the final radial location, $r_f$, after time t can be obtained as:

$$\int_{r_i}^{r_f} r\,dr = \int_0^t -\frac{Z_p V_i e^{\left(\frac{t'}{\tau}\right)}}{\ln\left(\frac{r_2}{r_1}\right)} dt' \quad [7]$$

where the initial DMA central rod voltage, $V_i$, corresponding to the initial particle position, $r_i$, is $$V_i = V_0 e^{\left(\frac{t_i}{\tau}\right)}, \quad [8]$$

where $t_i$ is the time at which the particle is injected. From Equations [7] and [8], the radial position of the particle at time t is:

$$r_f^2 = r_i^2 - \frac{2Z_p V_i \tau}{\ln\left(\frac{r_2}{r_1}\right)}\left(e^{\left(\frac{t}{\tau}\right)} - 1\right). \quad [9]$$

Alternately, the time taken to reach the final radial location $r_f$ from the initial radial location $r_i$ can be determined as:

$$t = \tau \ln\left[\frac{r_i^2 - r_f^2}{2Z_p V_i \tau}\ln\left(\frac{r_2}{r_1}\right) + 1\right]. \quad [10]$$

For a starting radial location, $r_i$, the particle residence times in the classification region, $t_1$ and $t_b$ corresponding to final radial locations of $r_1$ and $r_b$, respectively, can be calculated using Equation [10]. The axial locations of particles after times $t_1$ and $t_b$ can be obtained by solving Equation [3]. For an initial axial location assumed to be zero, the axial location at time t is given as:

$$z = Akt - A\alpha\tau\left(e^{\left(\frac{t}{\tau}\right)} - 1\right) + \frac{B}{2}t\ln(k) - \frac{B}{2}\int_1^{\frac{1}{k}\left(k - \alpha e^{\left(\frac{t}{\tau}\right)}\right)}\frac{\ln(t')}{1-t'} dt' + Ct + D, \quad [11]$$

where the constants $\alpha$, k, D are:

$$\alpha = \frac{2Z_p V_0 e^{\left(\frac{t_i}{\tau}\right)}\tau}{\ln\left(\frac{r_2}{r_1}\right)} \quad [12]$$

$$k = r_i^2 + \alpha \quad [13]$$

and $$D = \frac{B}{2}\int_1^{\frac{1}{k}(k-\alpha)}\frac{\ln(t')}{1-t'} dt' \quad [14]$$

The integral term in Equations [11] and [14] is the dialogarithmic function which can be estimated algebraically. The algorithm to solve this function is given in Ginsberg et al. (See Ginsberg, E. S. and Zaborowski, D. (1975) The Dialogarithm Function of a real argument, Communication of the ACMs, 18:200-201 hereby incorporated herein by reference.). For residence times, $t_1$ and $t_b$, the corresponding axial locations, $z_1$ and $z_b$, respectively, can be obtained using Equation [11]. For a DMA classification length of L, a particle is assumed to be sampled if its axial location satisfies the condition, $z_1 > L > z_b$. The residence time of the sampled particles is obtained by solving Equation [11] for different times, t, in the range of $t_b < t < t_1$. The exact time (within acceptable range of accuracy) when the particle reaches the sample exit is the residence time $t_r$ corresponding to that trajectory. The particle arrival time at the sample location with respect to the scan start time is the sum of the residence and injection times i.e. $t_f = t_r + t$.

To calculate the DMA transfer function, a large number (n) of trajectory calculations are required corresponding to a wide range of initial conditions. In our calculations, particles are injected at 50 different equidistant inlet radial locations at small time-steps of 1 ms. To ensure that the selected particle spatial distribution results in their uniform concentration across the aerosol inlet, the particles are weighted according to their local flowrates. The weight factors, $w_i$, are calculated as:

$$w_i = \frac{v_i r_i}{\sum_{j=1}^{n} v_j r_j} \quad [15]$$

Thus for N particles injected per unit time, the concentration across the aerosol inlet is $N/(2\pi v_i r_i dr)$, where $v_i$ is the velocity corresponding to the radial injection $r_i$ and dr is the uniform spacing between injection locations. Thus, the weighted concentration an injection location is given as:

$$w_i \frac{N}{2\pi v_i r_i dr} = \frac{N}{2\pi dr \sum_{j=1}^{n=50} v_j r_j} \quad [16]$$

Figure 3:
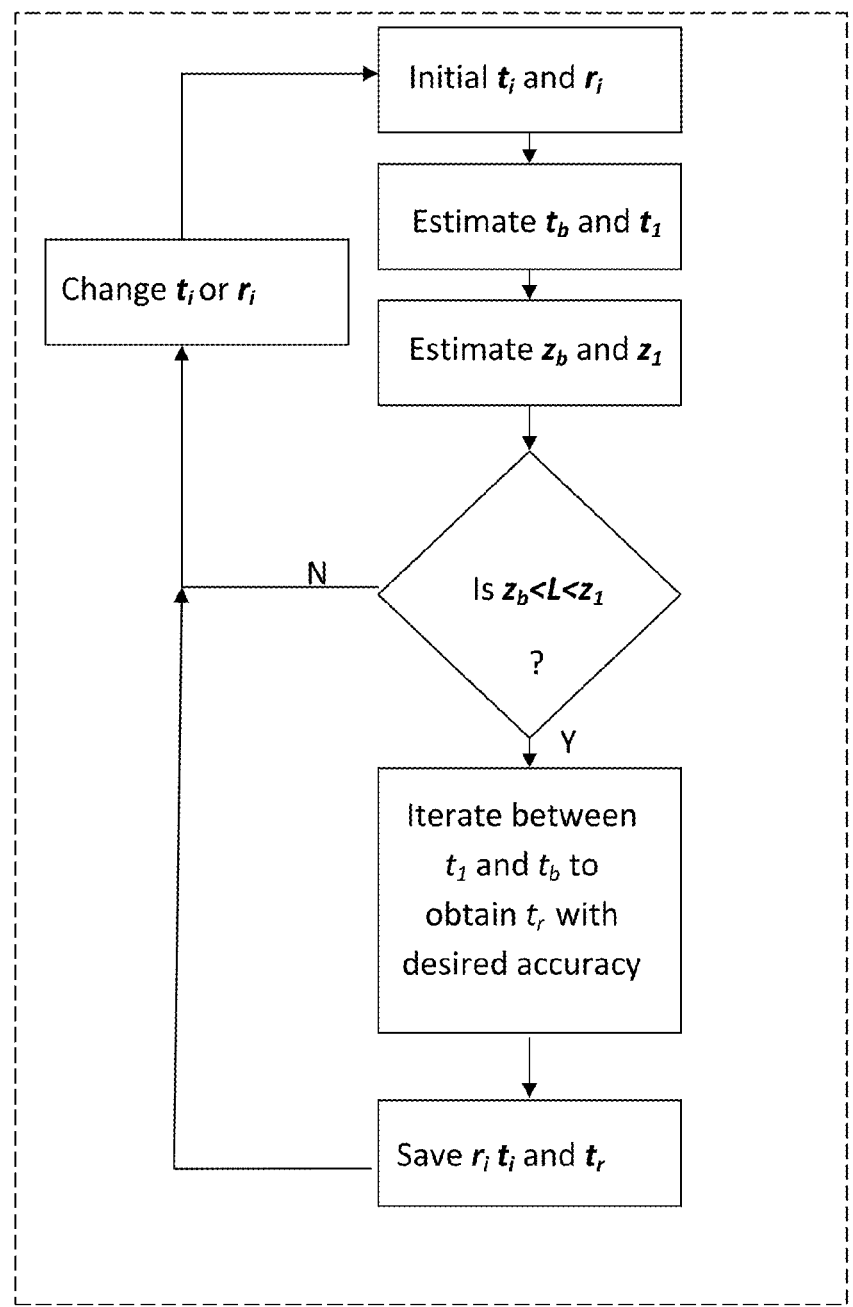
FIG. 3 illustrates a flow chart of trajectory calculation.

The right hand side of Equation [16] is constant for all injection locations and thus the use of the weight factor results in an uniform particle concentration across the aerosol inlet The procedure outlined above is used to calculate the arrival times and concentrations of particles at the exit of the classification region. A flow chart of the calculation procedure is shown in FIG. 3. Since Equation [11] cannot be inverted i.e. residence time cannot be explicitly expressed as a function of axial distance, the calculation procedure outlined in the flow chart is required to estimate particle sampled as well its residence time in the classification region. The arrival times of particles is then compiled to determine transfer functions using the approach described below.

Arrival-Time Transfer Function (ATF) and Scanning DMA Transfer Function

To determine the scanning DMA transfer functions, the trajectory equations are solved to obtain a data set of residence time, injection time, and injection location of sampled particles. The sampled particles are binned into different time bins (also called counting interval) based on their arrival time. For a selected counting interval, the number of particles arriving at the sample port is determined. The counting interval is chosen such that it is larger than the injection time interval but small enough to capture the transfer function accurately. For the present calculations, an injection time interval of 1 ms and a counting interval of 50 ms are used. For equal aerosol and sample flows, the sampled particle concentration fraction in a selected counting interval is determined as the ratio of number of particles sampled to the number injected over the same time interval. Particles counted in that particular time interval are multiplied by their corresponding weight factor. For a selected particle electrical mobility, the sampled concentration fraction as a function of time is referred to as the Arrival-time Transfer Function (ATF).

Figure 4:
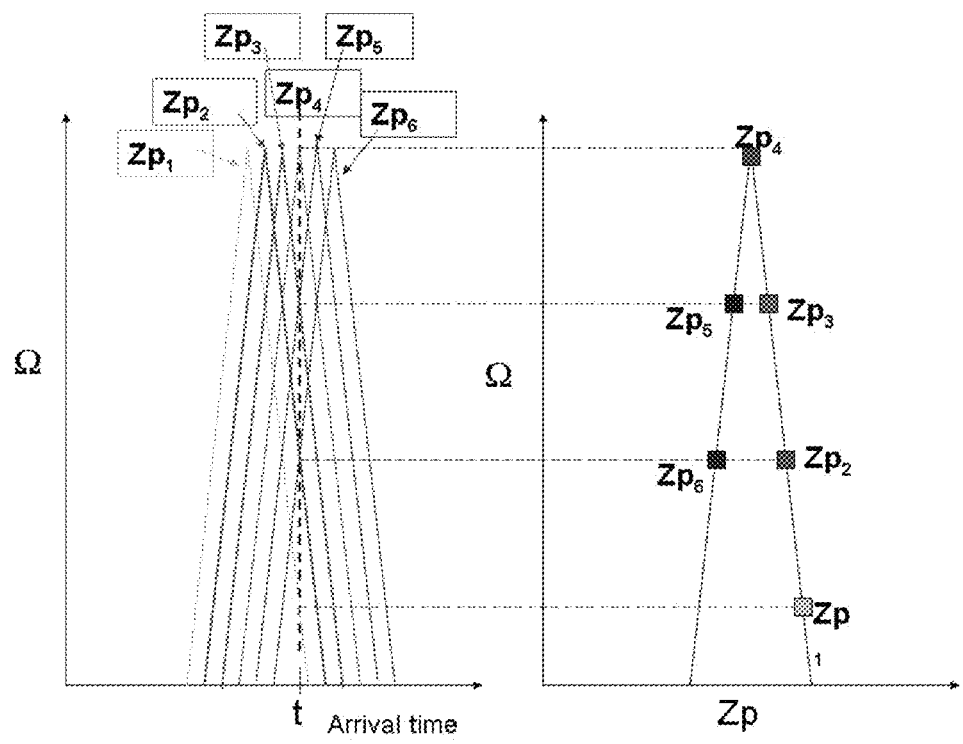
FIG. 4 illustrates a determination of electrical-mobility based transfer functions from ATF for different electrical mobilities over a given counting interval.

The scanning DMA electrical-mobility transfer function (hereafter referred to as just the scanning DMA transfer function) is obtained as the sampled particle concentration fraction of different mobilities over a selected counting interval. At a selected sampling time, the sampled concentration fraction of particles of different mobilities can be determined from their ATF as illustrated in FIG. 4. FIG. 4 illustrates the determination of electrical-mobility based transfer functions from ATF for different electrical mobilities over a given counting interval. The ATFs of different mobilities are calculated using the procedure shown in FIG. 3 and for a given counting interval (time bin) the sampled fraction of different mobilities is obtained from the ATF to determine the mobility based transfer function.

Figure 5:
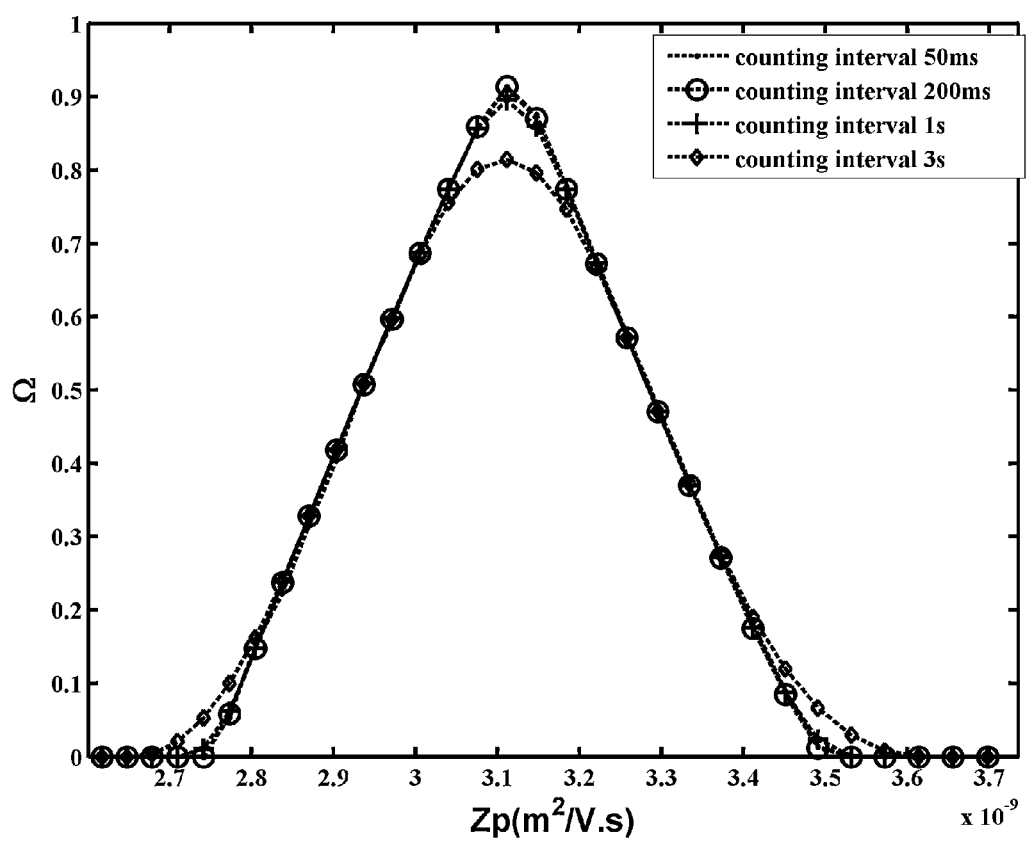
FIG. 5 illustrates a transfer function calculated for a scan time of 300 s for varying counting intervals.

The choice of counting time interval is important in the calculation of the scanning DMA transfer function. Larger counting intervals broaden the transfer functions and reduce their peak heights. The scanning DMA transfer functions obtained from the ATF calculation for a scan time of 300 s and varying counting intervals is shown in FIG. 5. FIG. 5. illustrates the transfer function calculated for a scan time of 300 s for varying counting intervals. For a counting interval of 3 seconds and larger, the transfer functions broaden slightly. The flow conditions used in the simulations are listed in Table 1. With this approach, the number of ATFs required to be simulated is the same as number of points required to determine the mobility-based transfer function. This method is, therefore, computationally expensive and real time transfer function calculation with this approach is not possible.

Simple Approach to Calculate Scanning DMA Transfer Function

An alternative approach to determine the scanning DMA transfer function is to transform the calculated ATF from a time-space to an electrical mobility-space. For an exponential voltage ramp, this transformation can be done theoretically without requiring repeated simulations. As explained in Wang and Flagan (1990), an exponential voltage ramp results in particle trajectories in the classification region that are independent of their injection times. Thus, as a function of time, the range of sampled mobilities will change but not the shape of the scanning DMA transfer function.

To convert from the ATF to the scanning DMA transfer function, consider two particles with electrical mobilities $Zp_1$ and $Zp_2$ related as:

$$Zp_2 = Zp_1 e^{\left(\frac{t'}{\tau}\right)}. \quad [17]$$

These particles will follow the same trajectory if their respective starting scan voltages, $V_1$ and $V_2$, are related as:

$$V_2 = V_1 e^{\left(\frac{-t'}{\tau}\right)}. \quad [18]$$

The two particles are identical in their behavior in the classification region, with a sample time difference of t'. This implies that the ATF of particles of different mobilities are same in shape, but shifted in their arrival times by t'.

Figure 6:
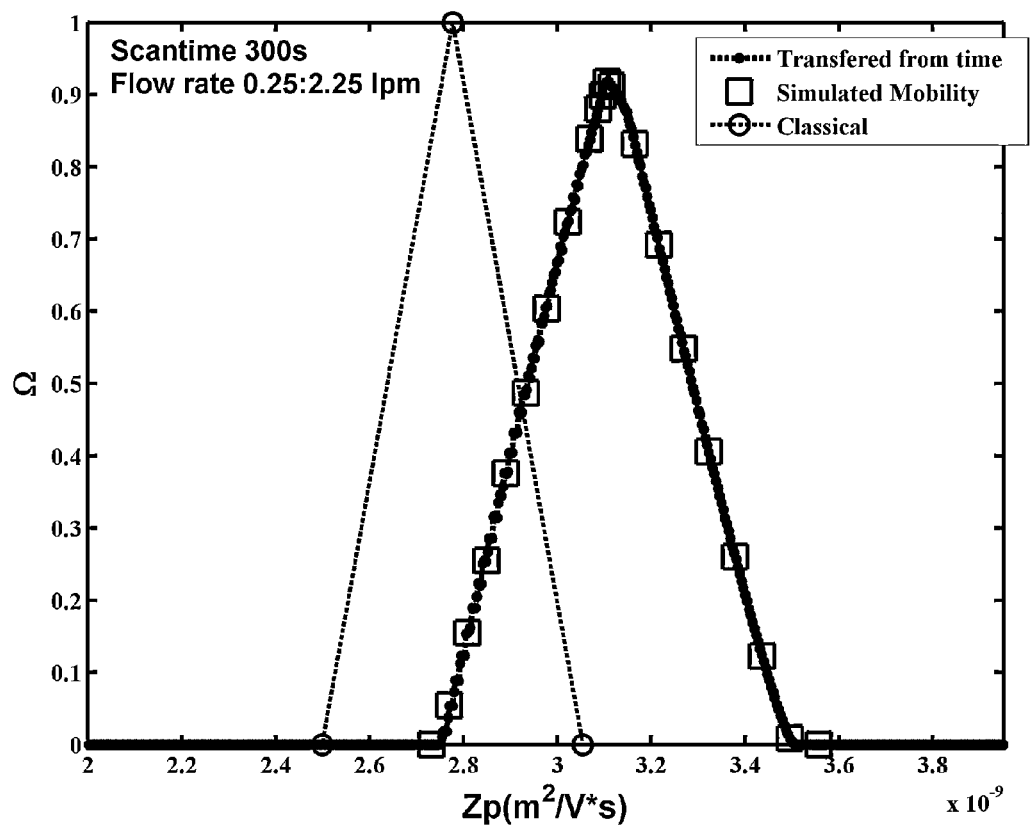
FIG. 6 illustrates a transfer function for 300 s scan, obtained by transforming from arrival time to electrical mobility, is compared to the transfer function calculated from ATF of a large number of particle mobilities.

The ATF of all mobilities can, therefore, be determined from the ATF of one mobility. The values of ATF of different mobilities at a given time for a counting interval $t_c$ can then be compiled to obtain the scanning DMA transfer function using the same procedure described in the previous section. This approach significantly reduces the computational time for scanning DMA transfer function calculation. The transfer function obtained using this method for a scan time of 300 s for flow conditions listed in Table 1 is shown in FIG. 6. FIG. 6 illustrates the transfer function for 300 s scan, obtained by transforming from arrival time to electrical mobility, and is compared to the transfer function calculated from ATF of a large number of particle mobilities. The counting intervals for both cases are kept same (0.05 s). The classical DMA transfer function is also shown. The particle sample time for all transfer functions are the same. The shift in the location of classical transfer function is due to the finite particle residence time in the DMA classification region.

For this transformation to be possible, two important conditions must be satisfied:

$$V_2^{st} \geq V_0 \quad [19]$$

$$V_2^{end}\left(e^{\left(\frac{t_r}{\tau}\right)}\right) \leq V_{max} \quad [20]$$

where $V_2^{st}$ and $V_2^{end}$ are the start and end values of the DMA voltage range corresponding to the injection times of the sampled particles of mobility $Zp_2$. The first condition (Equation [19]) implies that the sampled particles should be injected after scanning starts. The second condition (Equation [20]) requires that the particles reach the sample exit before the scanning is completed. Mobilities that satisfy the above conditions have a fixed set of particle trajectories that contribute to their ATF and hence the same ATF shape.

Figure 7:
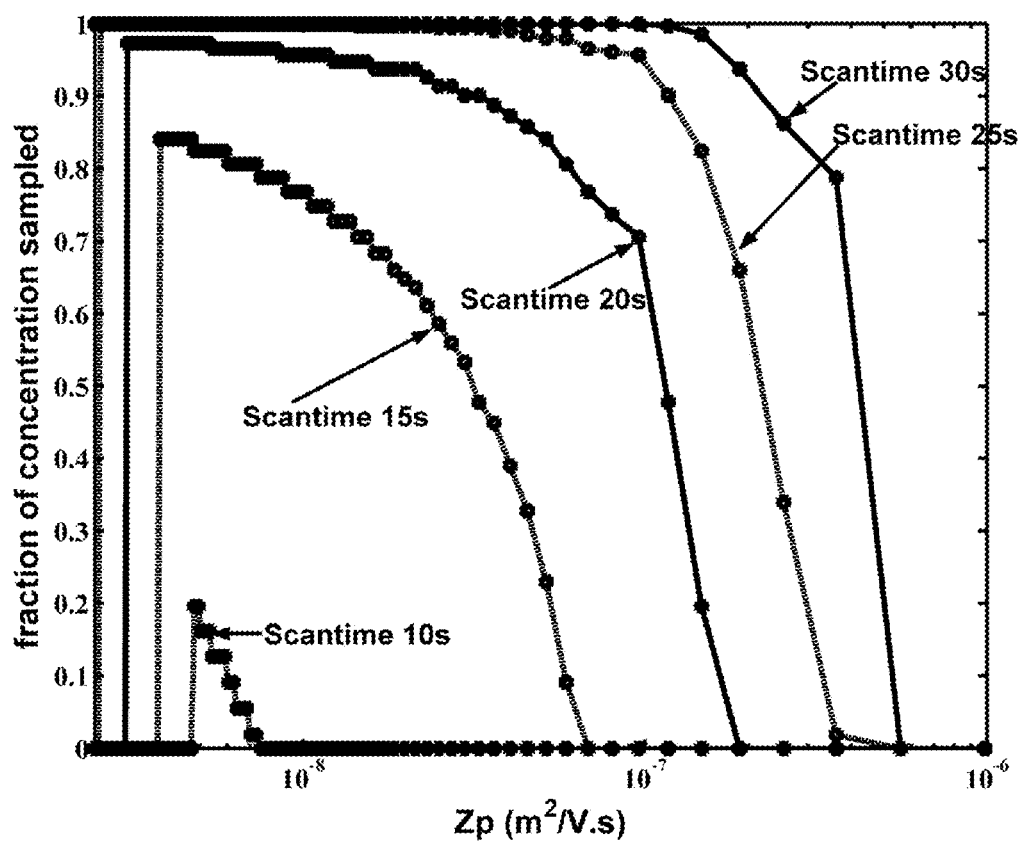
FIG. 7 illustrates a range of mobilities, satisfying the condition given by equation [20] for different scan times.
Figure 8:
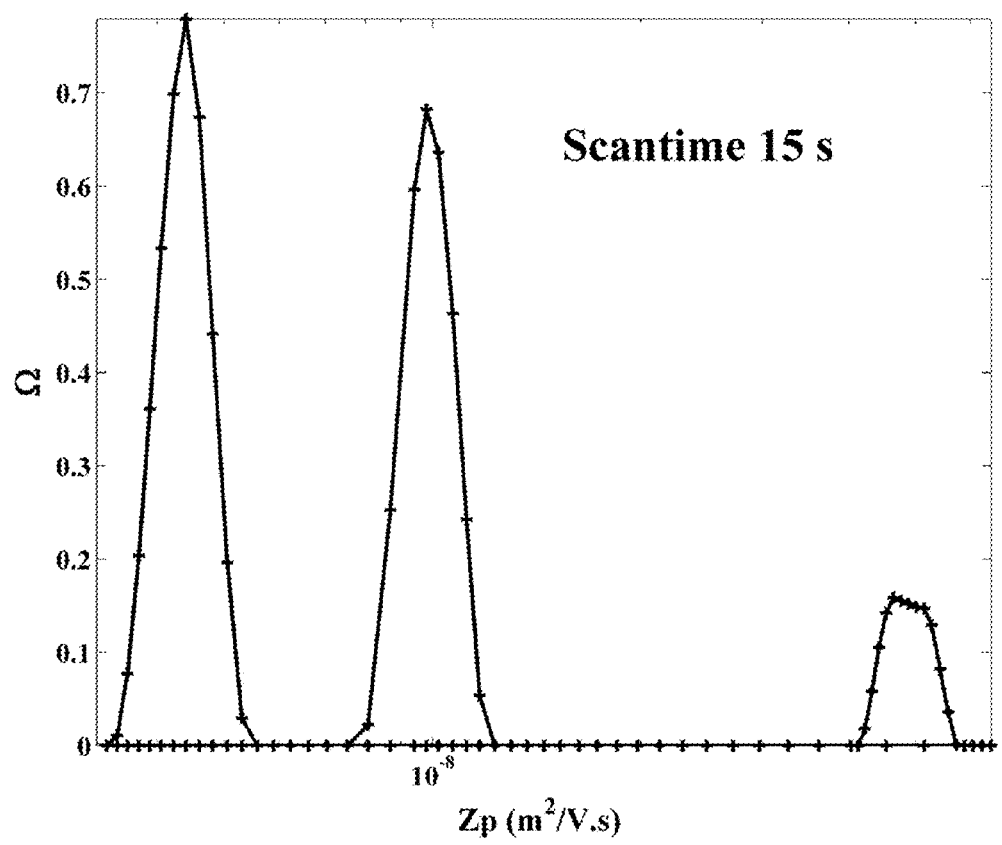
FIG. 8 illustrates a change in transfer function with mobility for very low scan time for the flow conditions given in Table 1.
Figure 9A:
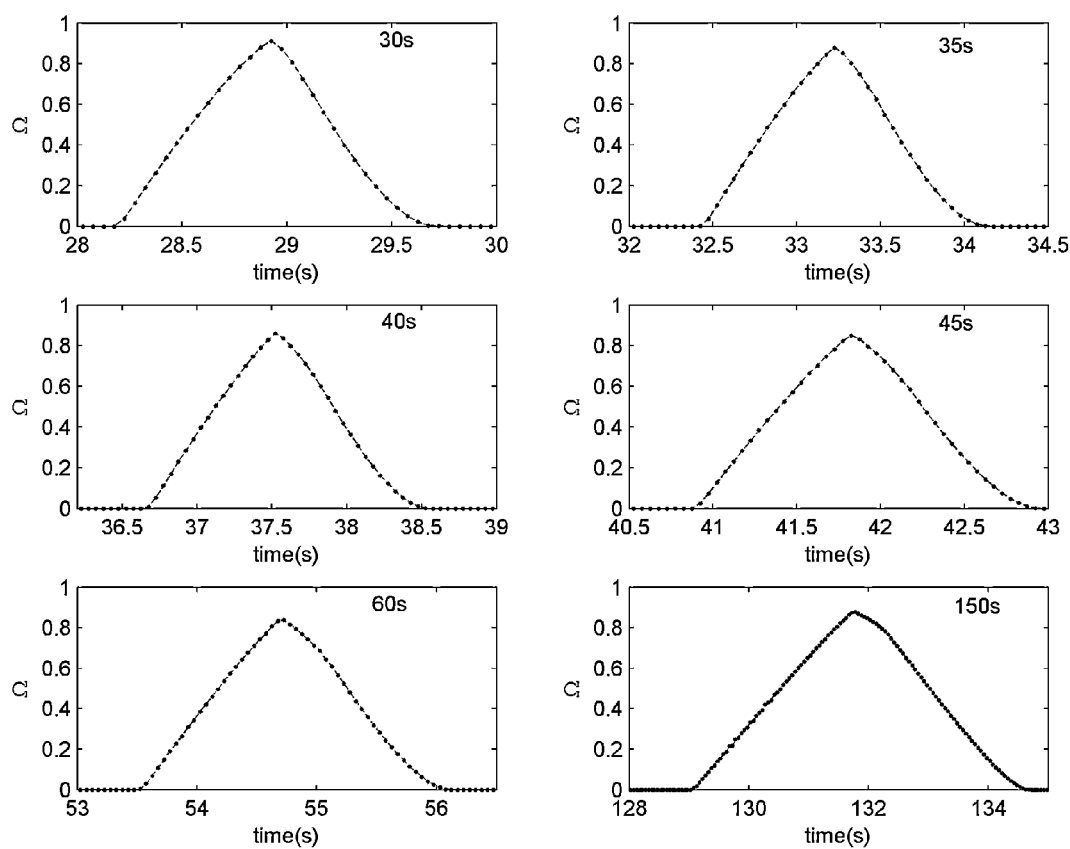
FIG. 9 illustrates the Arrival-time transfer function obtained for different scan times for 455 nm diameter singly charged particles.
Figure 9B:
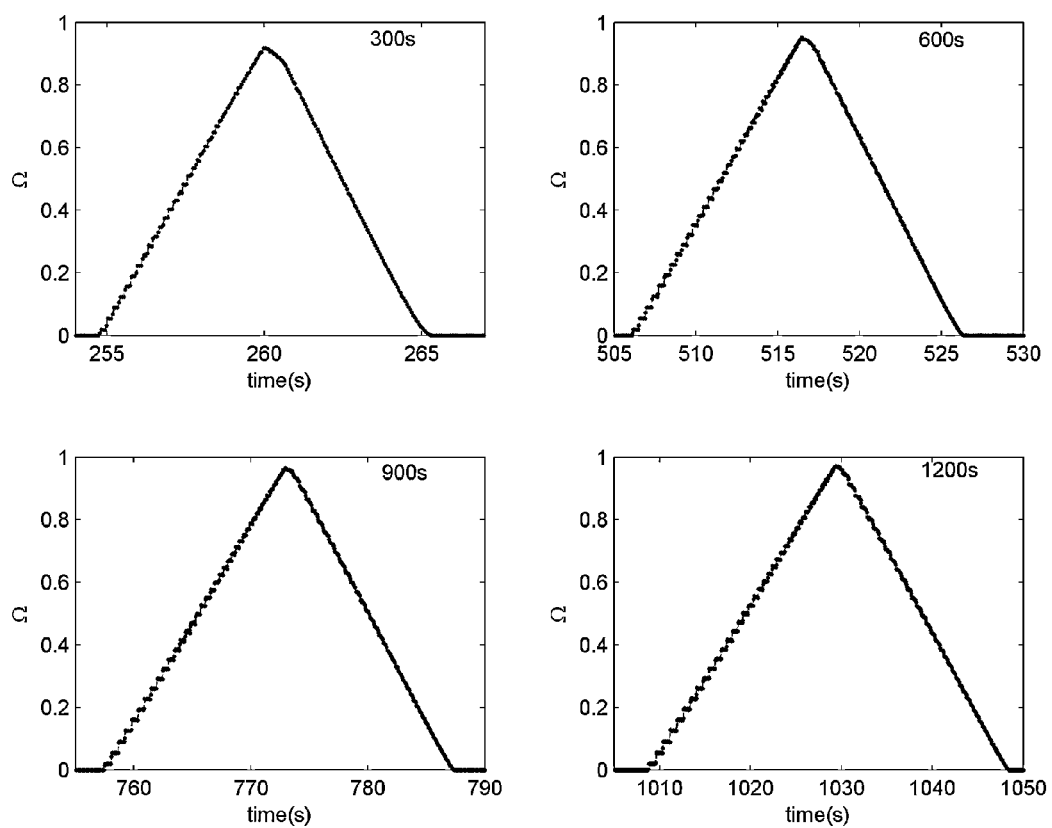

For some mobilities, depending on scan time and voltages, only a fraction of trajectories will satisfy condition [19]. For a very small scan time, e.g. less than 25 seconds for sheath and aerosol flowrates of 2.25 and 0.25 LPM respectively, none of the mobilities will satisfy these conditions. The ATF height of different mobilities relative to the ATF height calculated for a particle mobility satisfying condition [19] is shown in FIG. 7. FIG. 7 illustrates the range of mobilities, satisfying the condition given by equation [20] for different scan times. The flow conditions used for these simulations are given in Table 1. The effect of violating the condition given by Equation [19] results in decrease of sampled concentration of high mobility particles. The contribution from low mobility particles that do not satisfy Equation [20] is removed, resulting in a sudden drop in the curve for lower mobilities for some scan times. The y-axis values are the ratio of particle concentrations sampled without violating Equation [19] to the concentration sampled without considering the constraint of Equation [19]. Only those mobilities which have y axis value 1 in FIG. 7 satisfy Equation [19]. The mobilities which violate condition 20 has not been considered and given value 0. This causes the sudden drop in the curve for lower mobility regime for certain scan time in FIG. 7. For small scan times, particles of different electrical mobilities will be sampled at different fractions and hence the transfer function will not be independent of the sampled mobility range and this is illustrated in FIG. 8 for a 15 second scan time and flow conditions listed in Table 1. FIG. 8 illustrates the change in transfer function with mobility for very low scan time for the flow conditions given in Table 1. This change in transfer function is due to violation of condition [19]. For particles with electrical mobilities satisfying Equations [19] and [20], the ATFs are shown for different scan times in FIG. 9. FIG. 9 illustrates arrival-time transfer function obtained for different scan times for 455 nm diameter singly charged particles. The injection time interval for all cases is 1 ms and the counting interval is 50 ms. The flow conditions for these calculations are listed in Table 1.

Particles have a finite residence time in the classification region. During a scanning operation particles will, therefore, experience a range of voltages. Relative to the voltage required in a fixed voltage DMA to sample particles of a selected mobility, during upscan operation particles experiences a smaller voltage while they are at the inlet and a higher voltage while at the sampled exit. The particles that require voltage for fixed voltage operation above minimum voltage limit for scanning condition, but for up scan operation their voltage requirement at the aerosol inlet for being sampled is lower than minimum voltage, will violate Equation [19] and so have different shape of ATF relative to those particles that satisfy equation [19] and [20]. Decrease in the scan time increases the difference between voltage required for fixed voltage operation and voltage required at the inlet for scanning operation. Therefore, the range of high mobility particles that can be sampled in fixed voltage operation but violates the Equation [19] and so have different ATF shape for scanning operation, increases with the decrease in scan time. Thus, the range of mobility for which shape of transfer function does not changes with the mobility decreases with the decrease in scan time.

Figure 10:
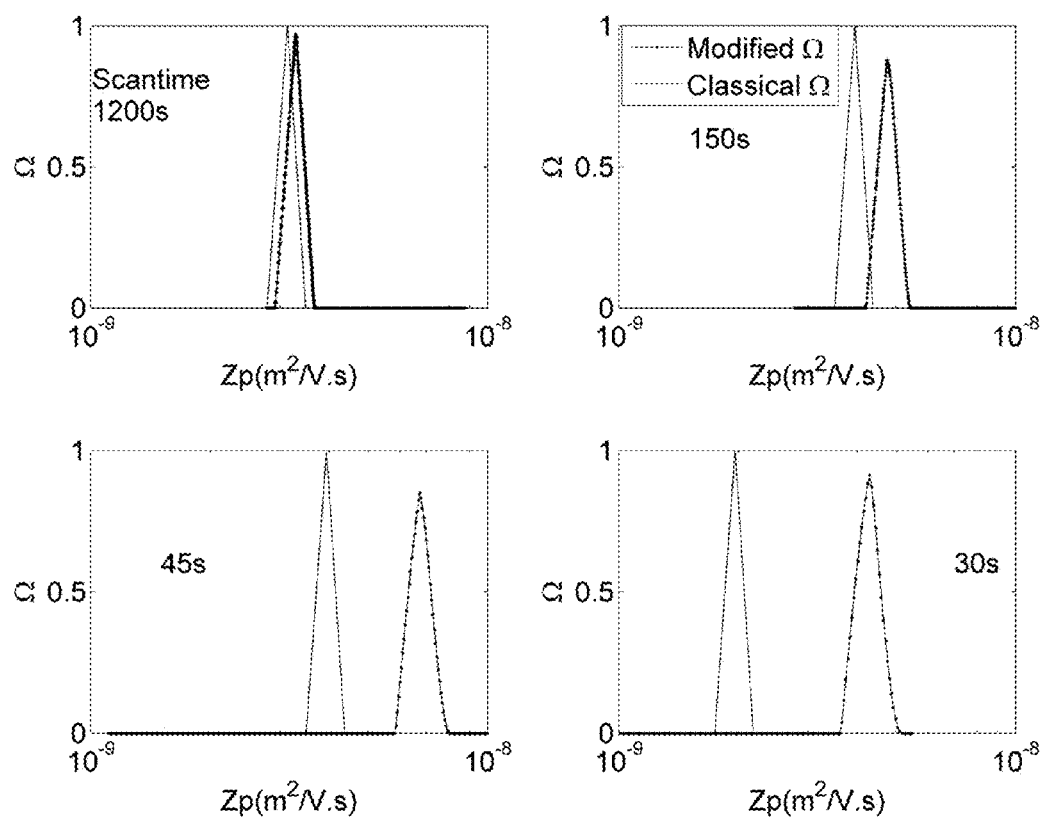
FIG. 10 illustrates, the calculated scanning DMA transfer functions compared to the triangular transfer functions for different scan times.

The effect of plumbing delay, because of the finite particle residence time in the classification region, is illustrated by comparison of the transfer functions of the scanning DMA and the classical DMA for different scan times (FIG. 10). FIG. 10 illustrates the calculated scanning DMA transfer functions compared to the triangular transfer functions for different scan times. The transfer functions are off-set as particle residence time in the classification region is neglected for the triangular transfer function. Zp* is derived based on the voltage corresponding to the time when particles reach the sample port in the classification region.

Figure 11:
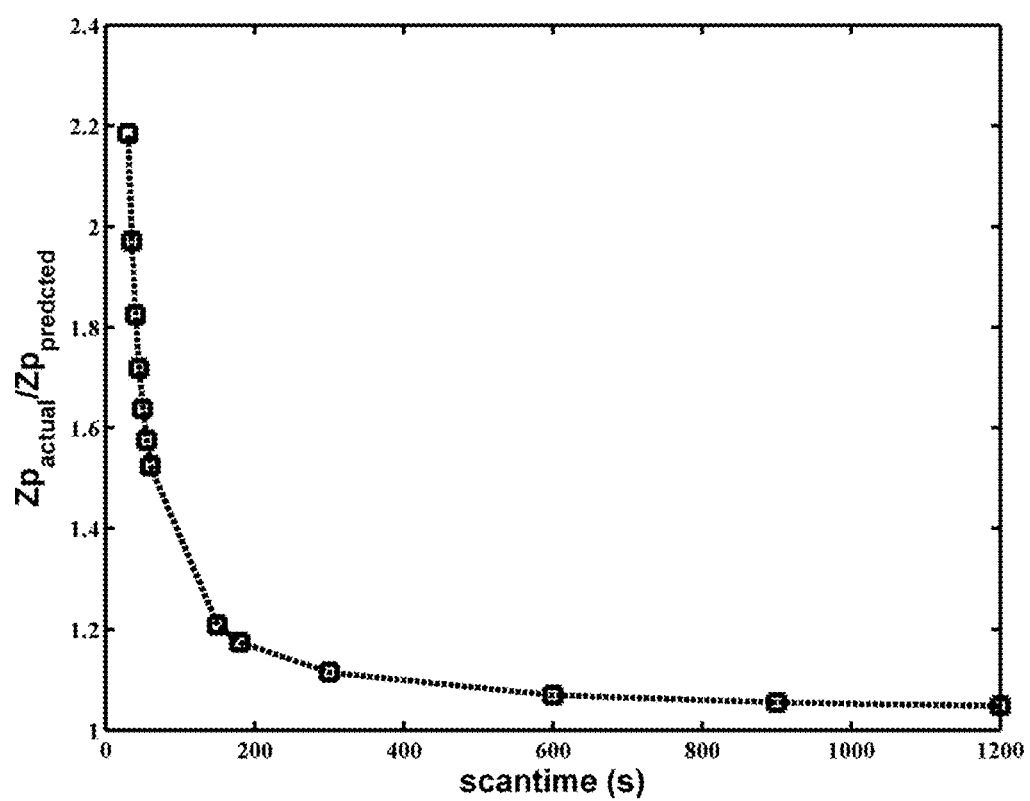
FIG. 11 illustrates a comparison of the mean sampled mobility values obtained from the scanning DMA and classical triangular transfer functions for varying scan times.

The comparisons show a shift due to plumbing delay associated with the DMA classification region flow and this shift increases as the scan time increases. The triangular transfer function of the classical DMA in FIG. 10 is determined considering central rod voltage at the time when the chosen particles exit the classification region. This voltage value will be larger than the mean voltage experienced by the particles in the classification region of a scanning DMA and thus the classical transfer functions will underestimate the electrical-mobilities of the sampled particles. The deviation of sampled electrical mobility ($Zp_{actual}$) from the one calculated based on the voltage value used to calculate the triangular transfer function ($Zp_{assumed}$) as a function of scan time is shown in FIG. 11. FIG. 11 illustrates a comparison of the mean sampled mobility values obtained from the scanning DMA and classical triangular transfer functions for varying scan times.

For fast scan times, the voltage increases rapidly in a given time interval, and thus the mobility-shift of the assumed triangular transfer function from the actual transfer function is much more than that for a slow scan operation.

Figure 12:
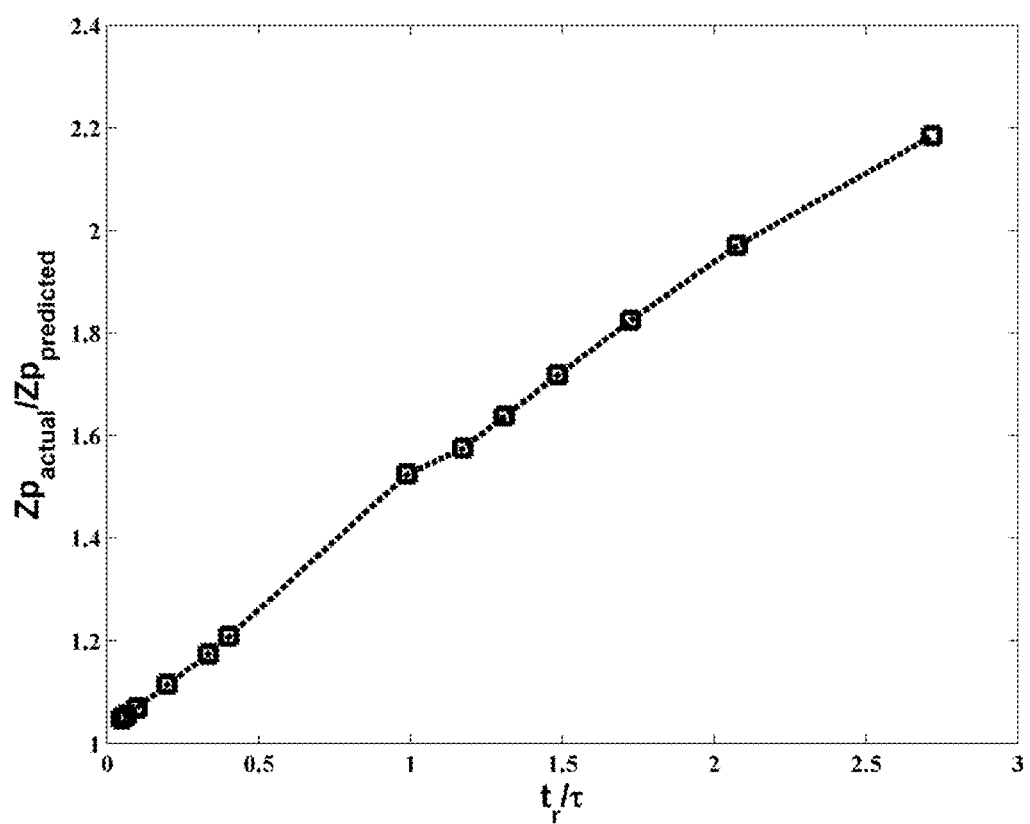
FIG. 12 illustrates the ratio of actual mobility sampled to the mobility predicted using classical DMA transfer function for varying residence times in the classification region.

FIG. 12 illustrates the ratio of actual mobility sampled to the mobility predicted using classical DMA transfer function for varying residence times in the classification region. The discrepancy between the actual sampled mobility to that predicted mobility (from the classical approach) increases with the increase in plumbing time in classification region.

Near Real-Time Transfer Function Calculation

For near real time scanning DMA transfer function calculation, the number of particle trajectory simulations required to obtain the ATF must be minimized. As illustrated in Collins et al. (2004), the DMA smearing during fast scan operation affects the up- and down-scan differently. During up-scan operation the DMA transfer functions are seen to have an approximately triangular shape, facilitating the development of a generalized approach to calculate transfer functions for different scan times. During down scan, however, the transfer function shapes vary significantly with scan time (Collin et al., 2004), thus complicating efforts to generalize the transfer function calculation for this operation. Thus, here only up-scan operation is considered.

A triangular ATF can be defined with four variables—three arrival times (corresponding to the vertices of the triangular) and the height of the ATF. Arrival time is the sum of the residence and particle injection times. For given flow conditions, DMA geometry, and particle mobility, the three critical arrival times corresponds to three critical trajectories. The arrival time of the lower mobility limit of the triangle corresponds to the trajectory starting from the inner radii of aerosol inlet to the outer radii of sample exit. The higher mobility limit of the ATF corresponds to the arrival time of the trajectory from the outer radii of the aerosol inlet to inner radii of the sample exit. The arrival time corresponding to the peak of triangle is seen to closely correspond to the arrival time of the trajectory starting from outer radii of aerosol inlet to the outer radii of the sample exit. Thus with these particular arrival times, three of the required variables can be estimated.

Figure 13:
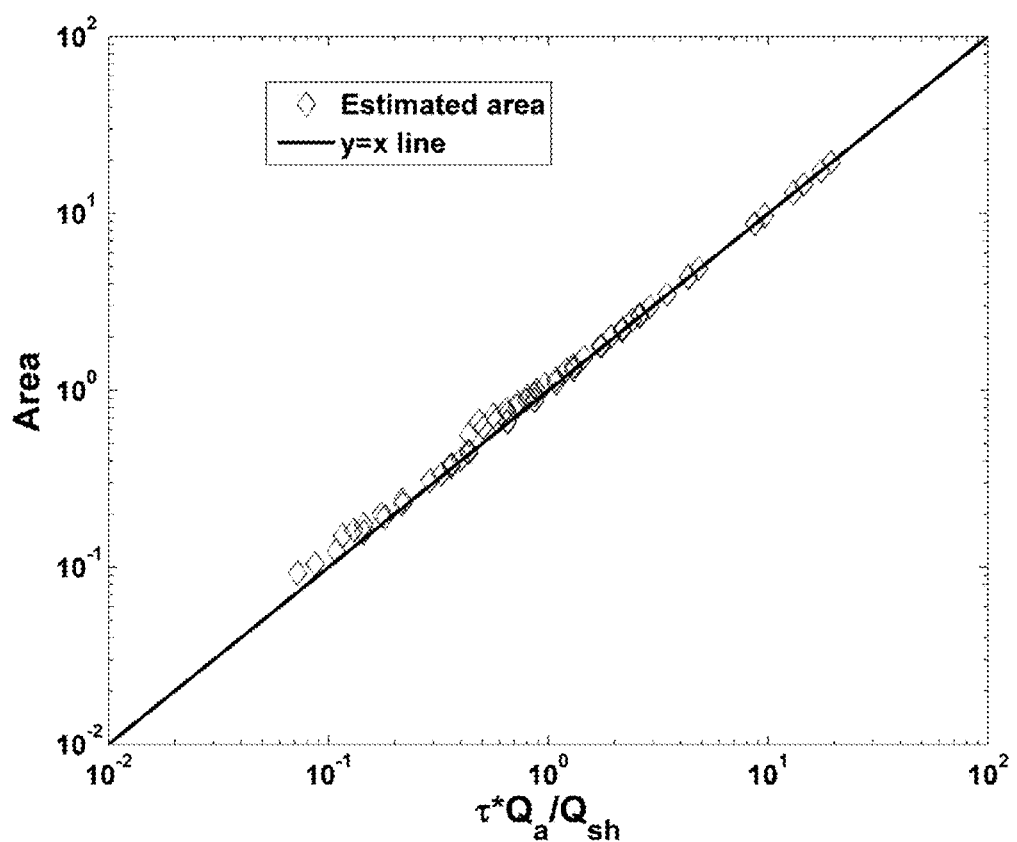
FIG. 13 illustrates a comparison of trend of area under ATF and $\tau^*$flow ratio.

The arrival times corresponding to the trajectories from the extrema of the aerosol inlet to the extrema of the sample exit can be determined as:

$$t_{(ab)} = t_{r(ab)} + t_{in(ab)}$$

$$t_{(2b)} = t_{r(2b)} + t_{in(2b)}$$

$$t_{(a1)} = t_{r(a1)} + t_{in(a1)}$$

$$t_{(21)} = t_{r(21)} + t_{in(21)} \quad [21]$$

where $t_{r\{\}}$ is the residence time for the different trajectories. For approximate ATF calculation, the three arrival times $t_{(ab)}$, $t_{(2b)}$, $t_{(21)}$ must be determined. The height of the ATF can be calculated from the area under the ATF. For a very slow scan, i.e., $(t_r/\tau) \to 0$, the area under the ATF was observed to be directly related to $\tau^*$flowratio (FIG. 13 illustrates a comparison of trend of area under ATF and $\tau^*$flow ratio is shown. It can be observed that for large values both of them are same), where $t_r$ is average residence time of the sampled particles, calculated as the algebraic mean of the four residence times $[t_{r(ab)}, t_{r(2b)}, t_{r(a1)}, t_{r(21)}]$. For fast scanning, i.e., when $(t_r/\tau)$ becomes significant, the simulation results suggest that the area under the ATF satisfies the relation:

$$\text{Area} = \tau * \text{flowratio} * \left(1 + k_1\left(\frac{t_r}{\tau}\right) + k_2\left(\frac{t_r}{\tau}\right)^2\right) \quad [22]$$

Figure 14:
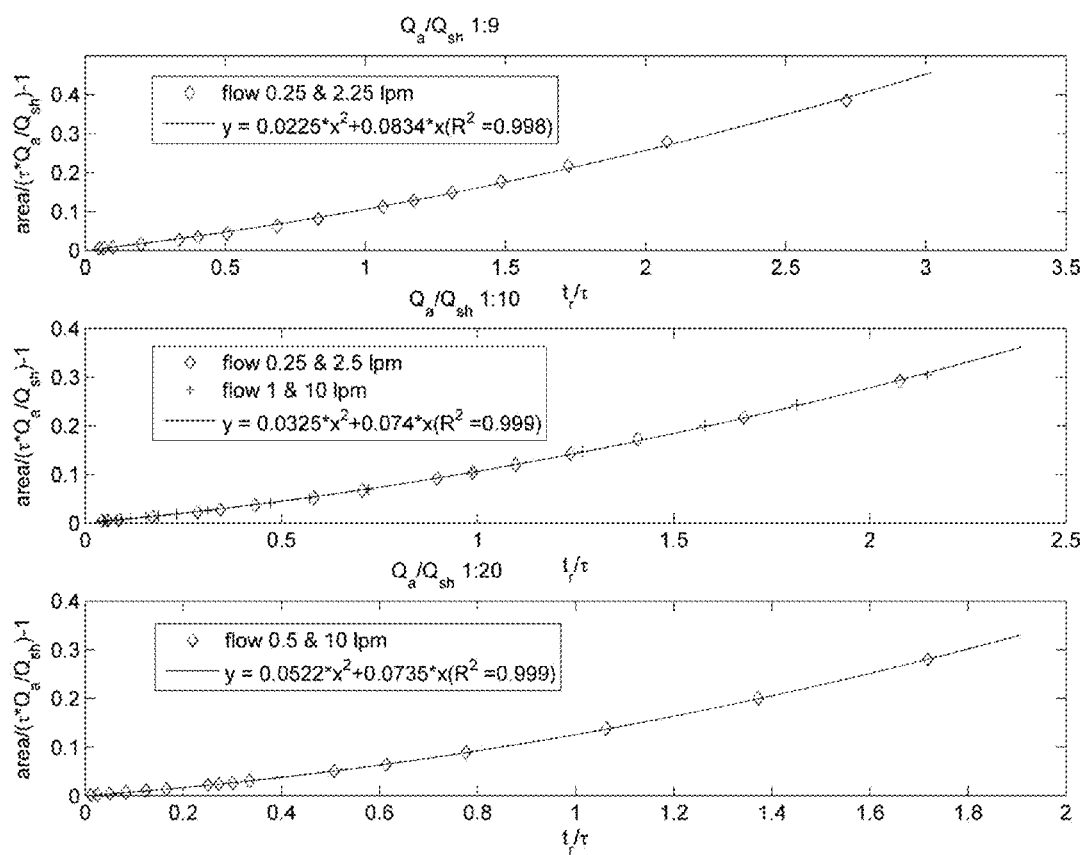
FIG. 14 illustrates the relationship between area under ATF to $\tau^*$flow ratio is seen to fit a second order curve to a good approximation.
Figure 15:
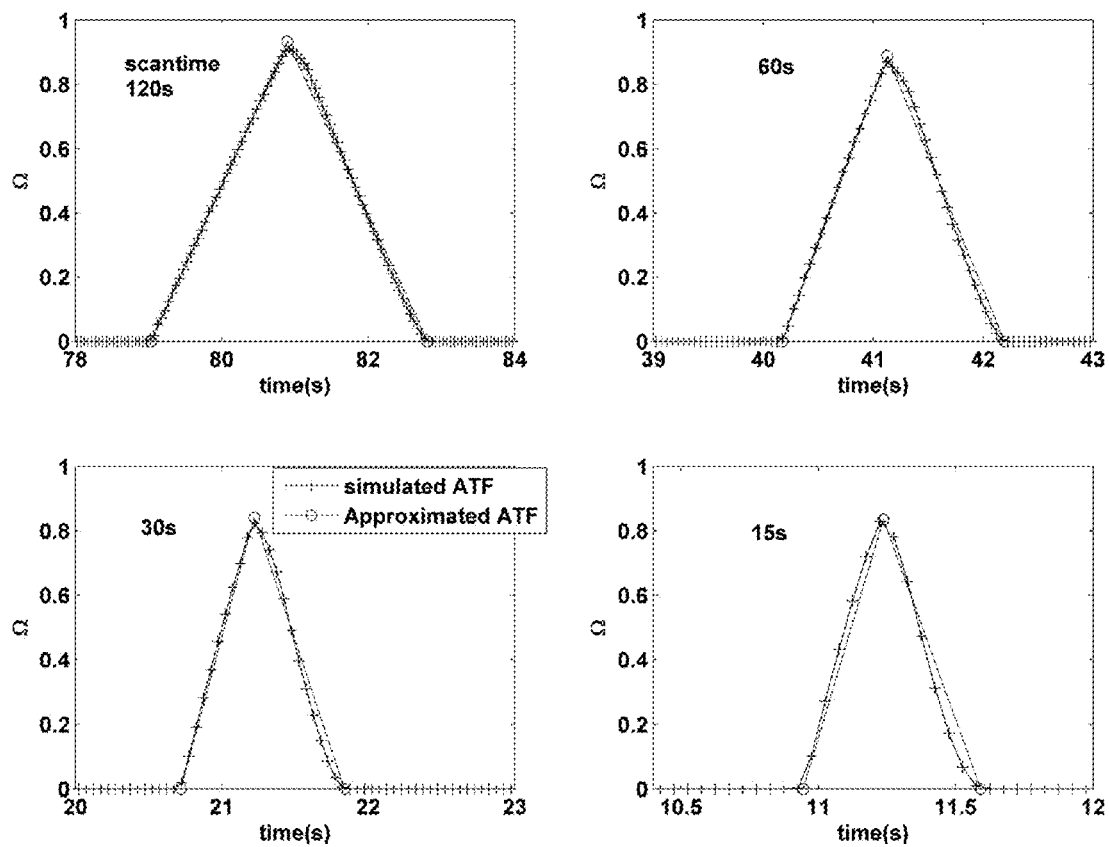
FIG. 15 illustrates the approximate triangular transfer function determined from the three critical trajectory simulation and area relation shown in FIG. 15 is compared with the actual ATF.

The constants $k_1$ and $k_2$ were obtained from a polynomial curve fit. Thus for a given DMA geometry and flow conditions, the area under the ATF for any scan time can be obtained by simulating the ATF for just two scan times. The ATF areas as a function of scan and residence times for flow ratios of 1/9, 1/10 and 1/20 are shown in FIG. 14. The values of $k_1$ and $k_2$ are seen to be constant for a selected flow ratio. Therefore using this relation, one can obtain the area under the ATF for any scan time for a given DMA geometry and flow condition. Using Equation [22] and $k_1$ and $k_2$ from FIG. 14, the approximate ATF for a flow ratio of 1:10, and a net flow of 6 LPM is shown in FIG. 15. FIG. 14 illustrates the relationship between area under ATF to $\tau^*$flowratio is seen to fit a second order curve to a good approximation. For a selected flow ratio, the coefficient of first and second order terms of $t_r/\tau$ are independent of the et flows. FIG. 15 illustrates the approximate triangular transfer function determined from the three critical trajectory simulation and area relation shown in FIG. 14 is compared with the actual ATF (determined by simulation procedure followed for FIG. 9). The approximated ATF matches well with the simulation result and thus the approximate method is suitable for near real time scanning DMA transfer function calculation.

A comparison of the approximate and numerically-simulated ATF shows that the approximate ATF is a good approximation to the simulated ATF. The height of the ATF is then obtained as Area/($t_{21}$-$t_{ab}$).

This suggests that for a given flow condition and for an electrical mobility range satisfying conditions of Equation [19] and [20], the simulation of only four trajectories and prior calculation of ATF for two particular scan times for the selected flow ratio is sufficient to determine the transfer function of all other scan times.

Experimental Evaluation of Fast-Scan Function

Figure 16:
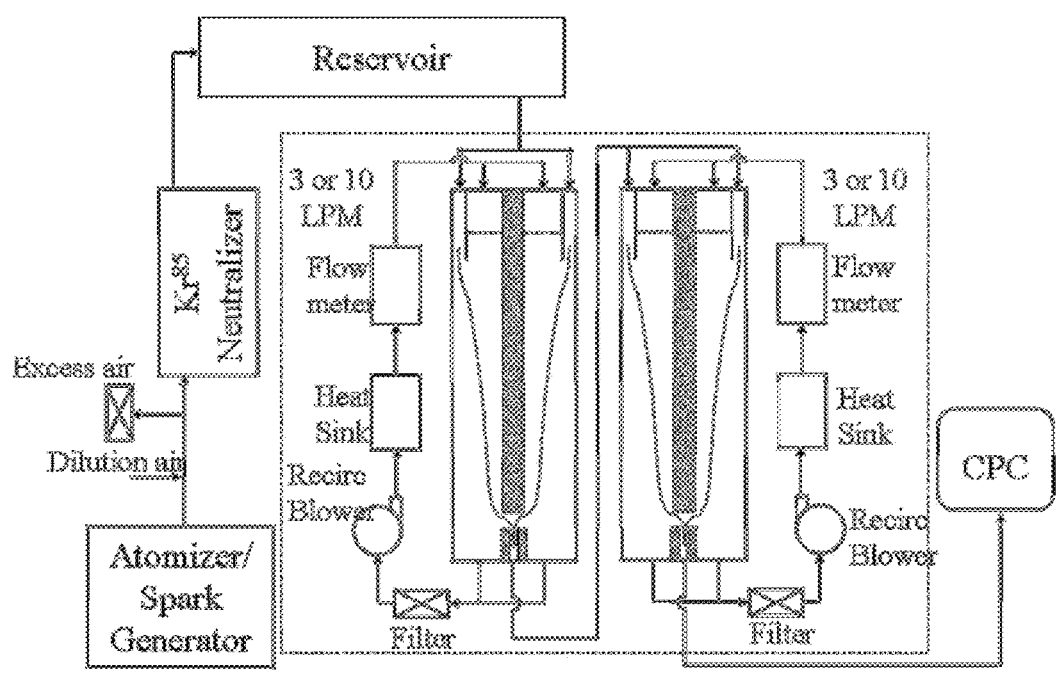
FIG. 16 illustrates the schematic diagram of the experimental setup used to obtain data for validation of modeling results.

To validate the calculated scanning DMA transfer functions, the experimental setup shown in FIG. 16 was used. A spark generator (PALAS GFG 1000) was used to generate the test aerosol and particle concentrations were maintained steady over time using a buffer chamber. A TDMA setup is used with long-column cylindrical DMAs and a TSI 3010 CPC as a particle detector.

The upstream DMA selects particles of a narrow mobility, while the second DMA scans the selected distribution at different rates. The use of the TDMA setup eliminates complications of dealing with the effect of particle diffusion on the instrument transfer functions. At fast scan times, size distribution measurements are complicated by transport plumbing delays between the DMA exit and the particle counter and also because of smearing in the CPC. To simplify comparison of modeling predictions with experimental results, only the area under the size distribution curve downstream of the TDMA is considered. While the CPC smearing will skew the concentration distribution over time, the skewed distribution will still have the same area as the undistorted distribution. The flow conditions used for this experiment are listed in Table 2. To avoid the problem of multiple charging, the analysis is based on particle electrical mobility.

As described previously, the area under the scanning DMA transfer function is a function of scan time as well as residence time, while for the triangular transfer function area varies only with scan time. The difference between the area of the two transfer function increases with the ratio of residence time to scan time. Thus for effective comparison, experiments were conducted with very low scan times, that were large enough to satisfy the constraints of Equations [19] and [20].

Figure 17:
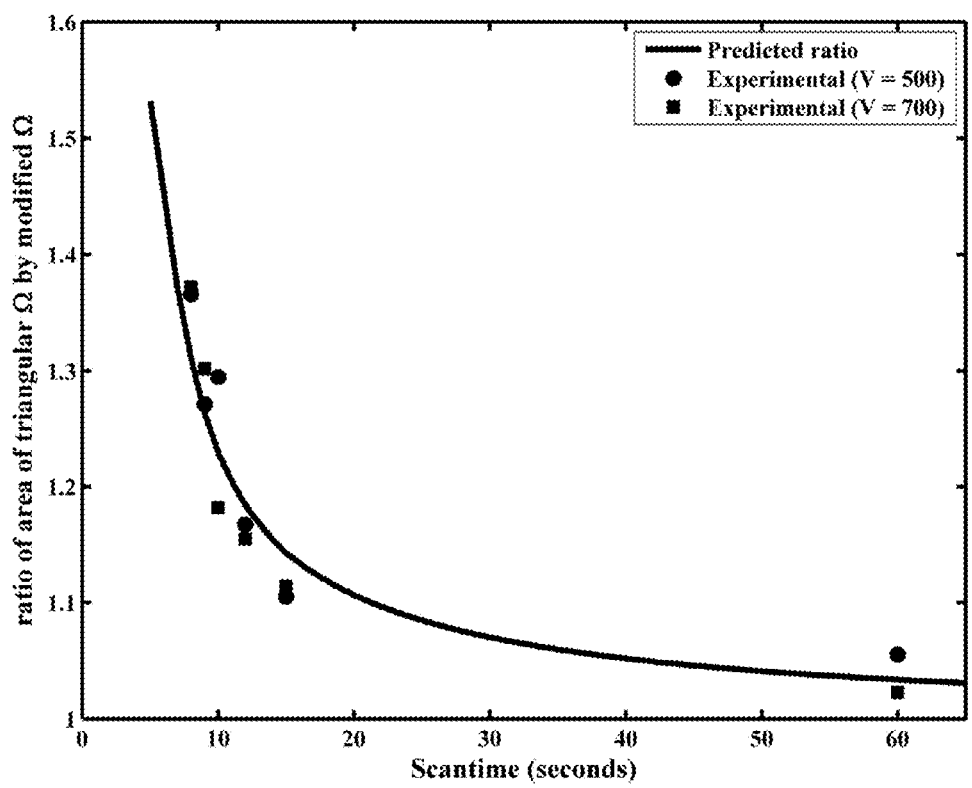
FIG. 17 compares the experimental results of area under the size distribution curve downstream of the TDMA setup with that predicted by the triangular and calculated scanning DMA transfer functions.

To obtain the size distribution downstream of the first DMA, the second DMA was scanned over 800 seconds and the collected concentration data was inverted using an L-curve regularization method. For this long scan time operation, the DMA transfer function was assumed to be triangular. The upstream DMA was used at the fixed voltage of 500 and 700 to minimize the effect of diffusion. The particles sampled in these voltage regime lies around 50-70 nm. The obtained particle number size distribution was then convolved with the classical triangular transfer function and the calculated scanning DMA transfer functions for scan times of 8, 9, 10, 12, 15, and 60 seconds. For these scan times, the conditions [19] and [20] were satisfied by mobilities with non-zero concentration at the inlet of second DMA. Since the convolved distributions do not include CPC smearing and the effect of plumbing delay, only the areas under the experimentally-obtained size distributions are compared with predictions based on the calculated scanning DMA and triangular transfer functions (FIG. 17 illustrates a comparison of the experimental results of area under the size distribution curve downstream of the TDMA setup with that predicted by the triangular and calculated scanning DMA transfer functions. The upstream DMA voltages used in this experiment are 500 and 700 V. For small scan times, it is predicted that the area under the transfer function will be much larger than that suggested by the classical transfer function and this is also observed experimentally. As the scan times are reduced, the discrepancy between the experimental results and the classical triangular transfer function is seen to increase and the experimental results closely match predictions based on the modified transfer function. This verifies the relation of area under transfer function and thus provides initial confidence that the new approach to calculate scanning DMA transfer functions from the ATF is valid.

Conclusion of Fast-Scan Function Discussion

The approximation of the scanning mode DMA transfer functions to be the same as the fixed voltage DMA will result in significant error when the DMA is operated in conditions corresponding to a large ratio of residence time to scan time. A new approach to obtain scanning DMA transfer functions using an arrival-time calculation is outlined. The scanning DMA transfer functions can be directly obtained from the arrival-time transfer functions. This approach results in an accurate calculation of scanning DMA transfer functions without requiring expensive Monte Carlo simulations. Preliminary experiments provide initial validation of the calculated scanning DMA transfer functions. The concept of ATF easily facilitates the eventual calculation of scanning electrical mobility spectrometer (SEMS) transfer functions, accounting for CPC smearing and transport plumbing delays.

TABLE 1

The DMA dimensions and flow conditions used in most simulations

| | |
|---|---|
| Length (cm) | L = 0.4444 |
| Inner radius (cm) | r1 = 0.937 |
| Outer radius (cm) | r2 = 1.958 |
| Minimum applied voltage (volts) | 10 |
| Maximum applied voltage (volts) | 10000 |
| Sheath flow and excess flow rates (LPM) | 2.25 |
| Aerosol and Sample flow rates (LPM) | 0.25 |

TABLE 2

The conditions used in the valuation experiments

| | |
|---|---|
| Sheath and excess flow rates of DMA 1 and DMA 2 (LPM) | 10 |
| Aerosol and Sample flow rates of DMA 1 and DMA 2 (LPM) | 1 |
| Minimum Voltage (V) | 10 |
| Maximum Voltage (V) | 10000 |

HD-DMA Apparatus

The second major portion of this disclosure discusses an HD-DMA apparatus used in conjunction with the Fast-scan Function analysis discussed above.

HD-DMA Design

A new instrument design for size segregation of particles at high resolution, based on their electrical mobility, is described here. It comprises of five flows, a polydisperse aerosol flow, a clean sheath flow, two monodisperse sample flows and a residual excess flow. The polydisperse aerosol flow can be in the range of 0.3-30 lpm. The two sample flows have the same flow range as the polydisperse flow. The sheath flows can be in the range of 10-300 LPM and will be generally chosen to be a magnitude higher (ten times) than the polydisperse aerosol flow. The sheath and polydisperse flows are introduced to a cylindrical classification region through hemispherical entrance regions. This design ensures laminar, uniformly-distributed flows entering the classification region. Particles are mobility-segregated in the classification region and the classified particles are sampled at two locations in the classification region. One of the locations is located closer to the entrance and sampler higher-mobility (smaller sized) particles, while the other location is towards the end of the classification region, and samples lower-mobility (larger) particles. All flows are maintained laminar in their channels, to avoid instrument performance degradation due to turbulence. The sample flows can be processed after being sampled from the classification region for counts (using a condensation particle counter) or charge measurement (using an electrometer) or collected on filters/impactors. The large sample flows ensures sufficient counts or charge measurement under typical ambient conditions, and permits fast scan measurements under low concentration conditions. High resolution measurements are possible because of the large sheath flowrates that are permissible in this instrument.

The instrument descrbed is used for size segregation of airborne particles based on their electrical mobility. Since the smallest sized particles have the greatest electrical mobility, this instrument is primarily useful sub-micron sized particles.

Ultrafine particles are important for various applications such as Nanotechnology (for their enhanced electrical and magnetic properties), environmental applications (for their health effects, climate change etc), and microelectronics applications (for nano particle contamination).

Several instruments are available to determine particles aerodynamic diameter, mass, optical property etc. These instruments are APS (Aerodynamic particle sizer), Impactor, AMS (Aerosol mass spectrometer), LPS (Laser particle spectrometer) etc. To determine particles electrical mobility size, some versions of Differential mobility analyzers have been developed (See Knutson and Whitby, 1975). Most of the currently available DMAs have sample flowrates of 1 LPM in the laminar regime (TS 3071, 3081, 3085 from TSI Incorporated). Some versions of DMAs have relatively high flow rates but also operate in very high Reynolds number flow regime, which is prone to turbulent flow with small instabilities. An example of this type of DMA is the Vienna DMA.

The commercially available DMAs have tradeoffs between Reynolds number and flow rates. While low Reynolds number is desired for better flow characteristics and particle losses, high flow rates are desired for a greater signal to noise ratio and thus measurement accuracy. The instrument disclosed here is aimed at providing relatively high flow rates while maintaining low Reynolds number. Also, multiple sample ports are located in the current design to classify particles over an extended nanoparticle size range. In addition, the instrument shown here has features that provide improved performance with respect to resolution of very small particles (<10 nm) and also avoids non-uniformities in electric field and flow mixing problems at the junction of aerosol and sheath flow.

For dynamically changing environments, real time determination of size distribution is required. The instrument shown here has reduced particle residence time in the classification region, and thus permits increased scan rate, and the provision of two sample ports provides more data per scan for a wide range of particle diameters, which enables capture of dynamics with improved accuracy.

Summary of the Instrument

To achieve the objectives of this instrument, several new features are introduced. First, the annular region of the classification region has a much greater radius while maintaining a narrow gap between the annular regions. The increase in the radius, increases the area of the classification region and that helps increase the flow rate of the DMA operation, while maintaining a low Reynolds number. The instrument described here can be used with more than 7 times the flow rate of the popular commercially available DMA (i.e., TSI 3071). The other advantage of greater radii of the annular classification region, while maintaining the gap between annular regions constant, is the reduction in residence time of particles in the classification region by a small amount. This reduction in residence time increases the resolution of transfer function by reducing the diffusion effect of the particles (Stolzenberg, 1988). The other major advantage of reduction in residence time is increase in the range of particle diameter classified during the scanning operation. Since particles have the finite residence-time in the classification region, the ratio of residence time to scan rate significantly affects the fast scanning operation (Dubey and Dhaniyala, 2008).

The second new feature of this instrument is the use of multiple sample ports. Multiple sample port has been previously designed for MDMA by Chen et al (2007) but their design cannot be used for fast scanning purpose due to DMA smearing. The sample ports designed here are in the inner radii of the classification region from where the sample flow is collected symmetrically and can be used for further processing. The symmetrical collection of the sample flow removes any smearing problem that can be associated with the DMA during the scanning operation. The advantage of having multiports is that this increases the range of particles diameters that can be sampled from this instrument. The range of diameters sampled by each port has an overlap region. While the range of particle diameter sampled exclusively by one port increases the range of the DMA measurement, the range of particle diameter sampled by both the ports increases the information about the particle concentrations during the single scan. This implies that in a single scan this DMA can provide twice the information about certain particle diameters. This feature enables one to capture particle dynamics with greater accuracy.

The other important design feature in the current instrument is the merge location of the aerosol and sheath flows. The aerosol flow entering the classification region has a very small component of velocity in the direction normal to the sheath flow. This enables the two flows to merge very smoothly avoiding flow disturbances near the junction. Additionally a very gradual increase in outer radii of the classification region at the junction of the two flows is used to prevent undesirable electric field non-uniformity at the flow junction.

The sample flows collected from the slit in the classification region, are gradually allowed to turn in the axial direction. Throughout the sample flow region, the flow is turned such that any undesirable flow recirculation is avoided and the Reynolds number in the sample flow region is always within the laminar flow regime.

At the entrance of the instrument, hemispherical shapes are used for gradual laminar, axisymmetric introduction of sheath and aerosol flows into the classification region. The relatively simple design of the clean sheath flow inlet and the excess flow exit makes it possible to circulate the excess flow to the sheath flow with an inline filter between the two ports. The low pressure drop design of the instrument permits the use of ordinary recirculatory blowers for the closed circuit flow between the sheath and excess ports.

Figure 18:
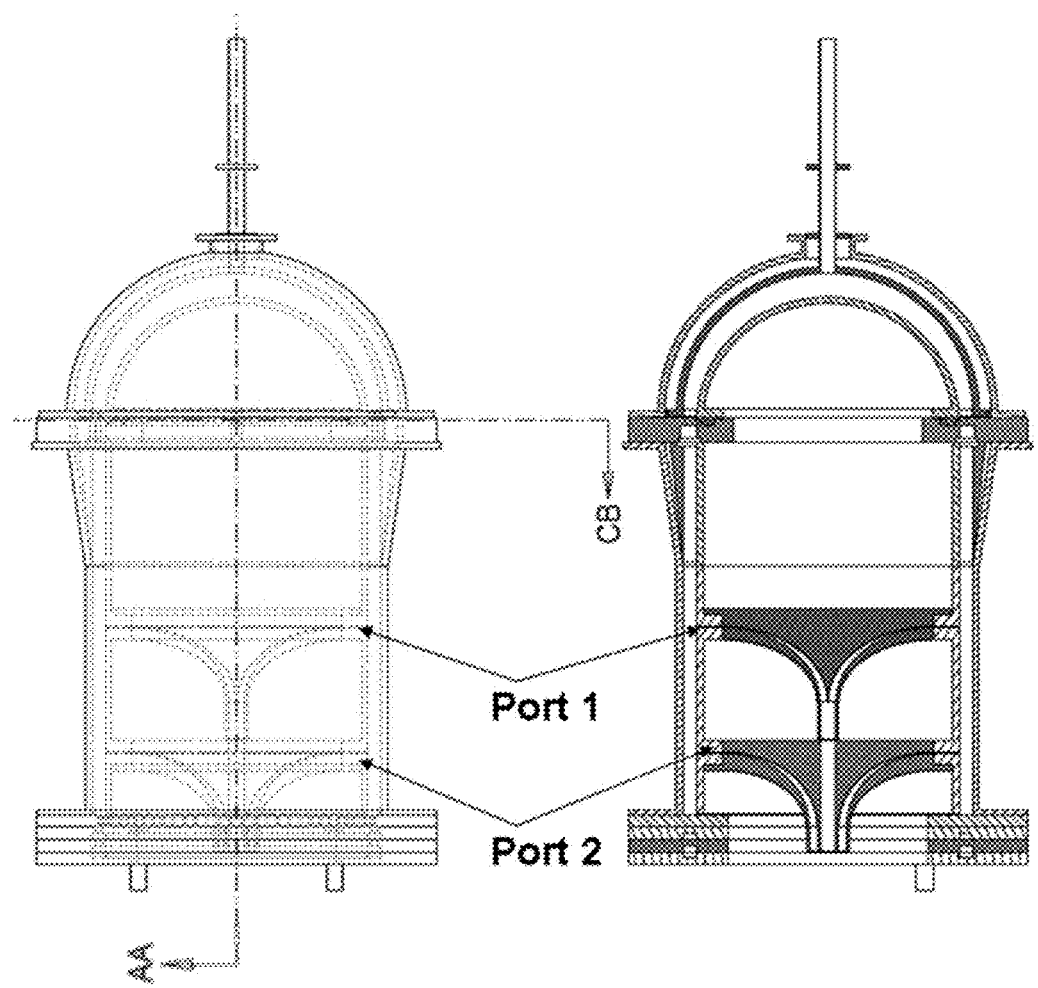
FIG. 18 illustrates sectional views of the HDMA.

FIG. 18 is a schematic of the HD-DMA. The section AA is the axi-symmetric section of the instrument. The section CB is the section showing the slot for aerosol flow and sheath flow before it enters the classification region or heads toward the merge of the two flows.

Figure 19:
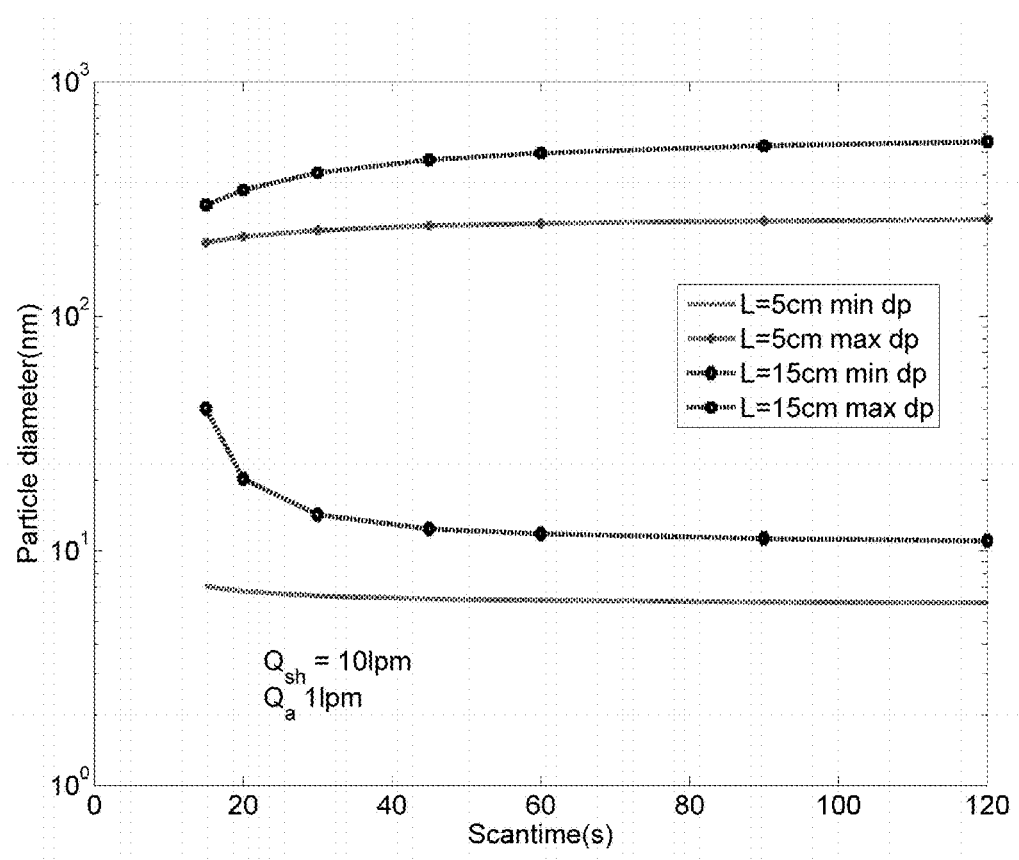
FIG. 19 illustrates the range of particle diameters that can be classified using the HD-DMA.

FIG. 19 illustrates the range of diameters that can be classified using the HD-DMA. The flow rate concerned in the plot are low flow rates and primarily useful for larger particles. As it can be observed a decrease in scan time decreases the range of particles that can be classified. The minimum and voltage for the scanning operation was kept at 10 and 10000 V respectively.

Figure 20:
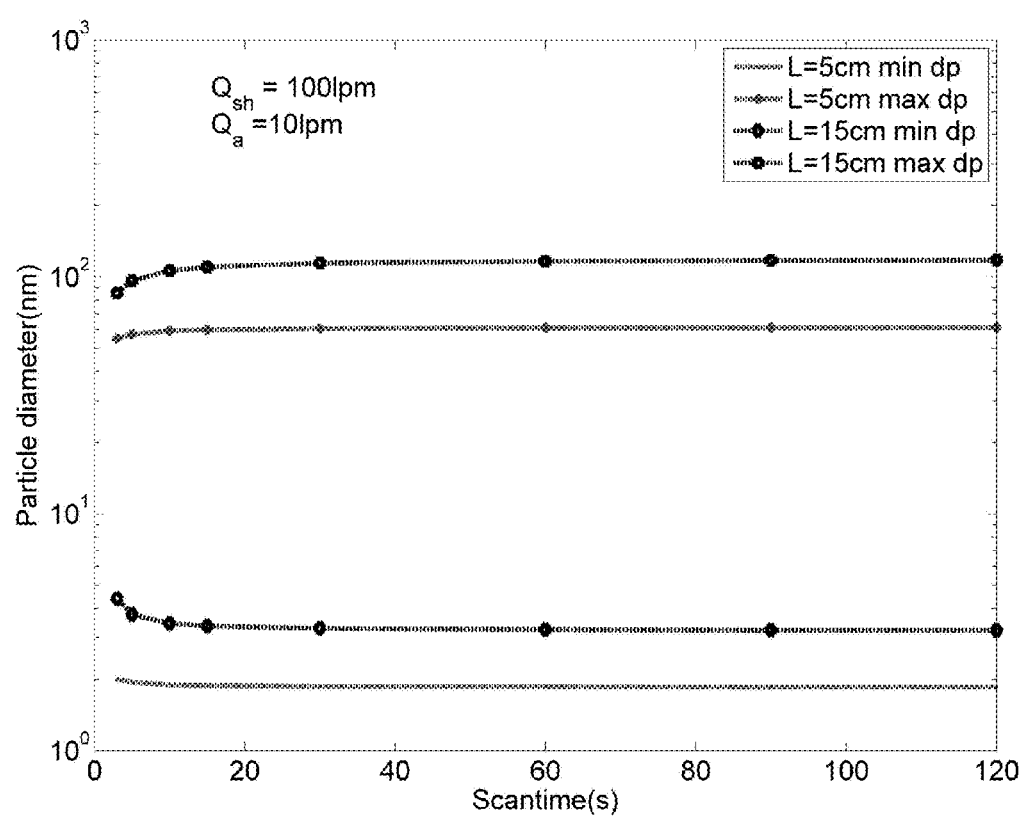
FIG. 20 also illustrates the range of particle diameters that can be classified using the HD-DMA.

FIG. 20 illustrates the range of particle diameters that can be classified using the instrument. The flow rate concerned in the plot is moderately high flow rates and is primarily useful for smaller particles. As it can be observed the decrease in scan time decreases the range of the particle that can be classified. The minimum and maximum voltage for scanning the operations kept at 10 and 10000 V respectively. It can be observed from the figure that for the range ~3 nm to ~50 both the ports (L+5 cm and L-15 cm) can sample the particles thereby increasing the data per scan.

Figure 21:
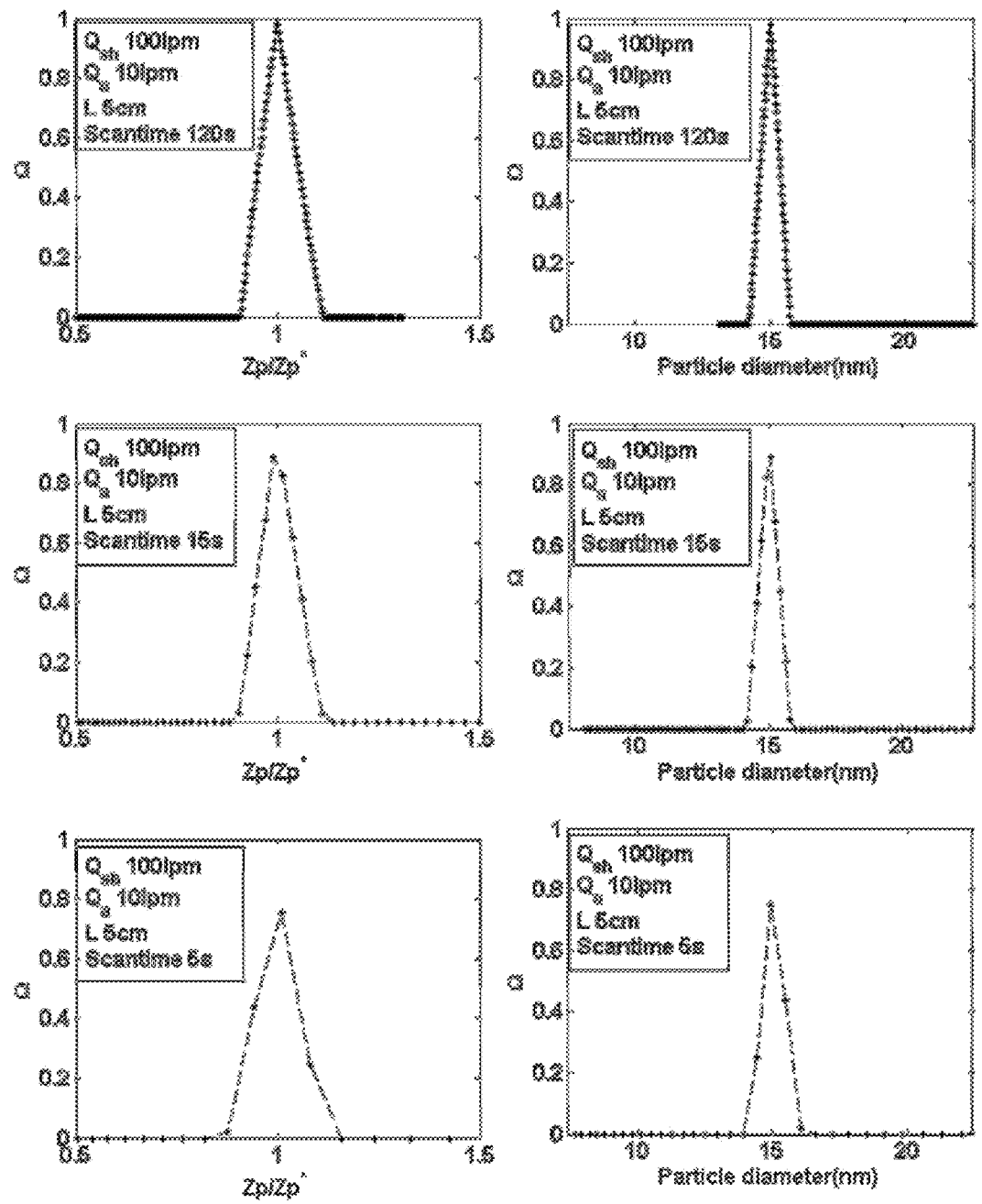
FIG. 21 illustrates mobility-based and diameter based transfer functions of the instrument.

FIG. 21 illustrates the mobility-based and diameter based transfer functions of the instrument. The transfer function is for the first sample port located at a distance of 5 cm in the classification region.

Figure 22:
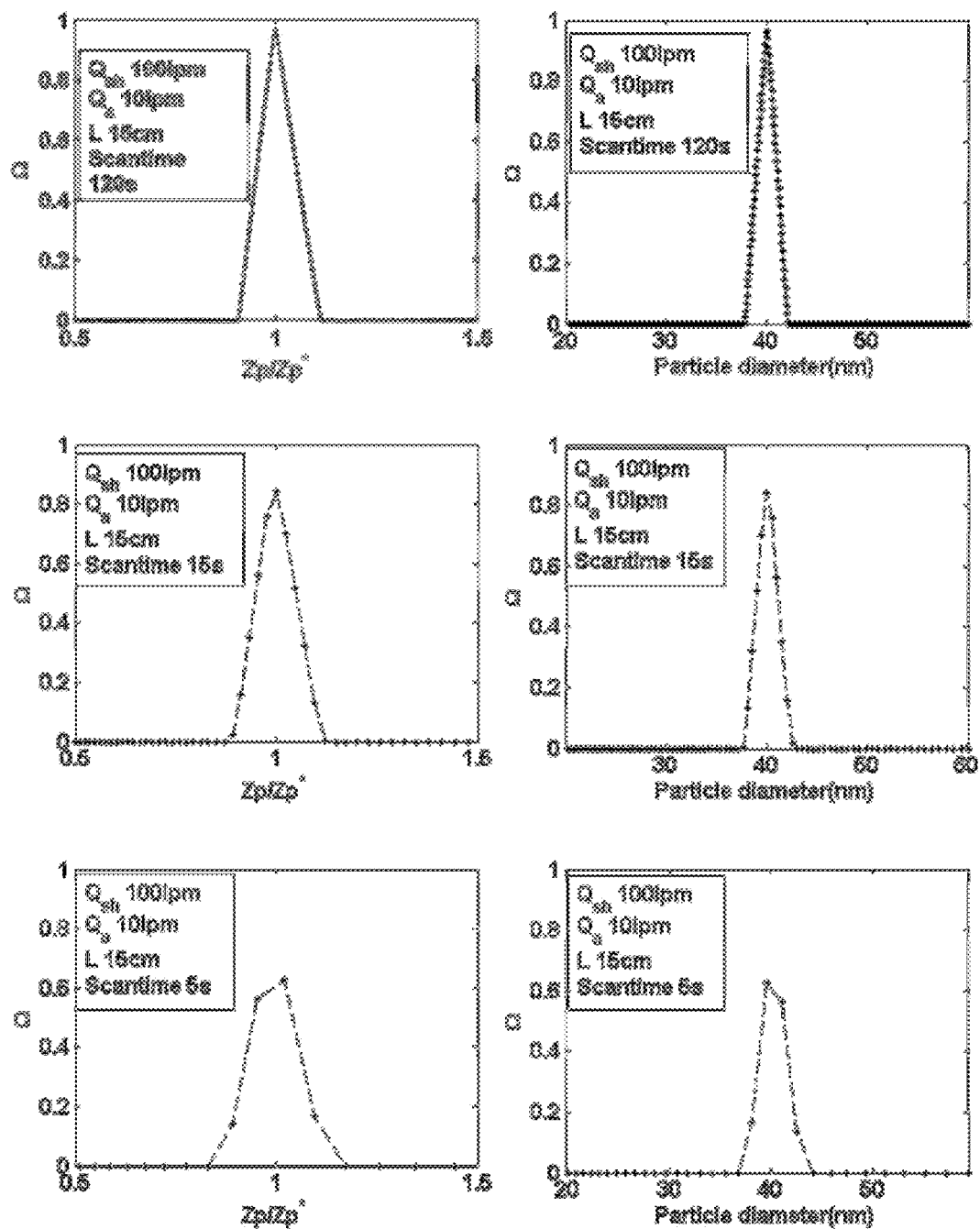
FIG. 22 also illustrates mobility-based and diameter based transfer functions of the instrument.

FIG. 22 also illustrates the mobility-based and diameter transfer functions of the instrument. The transfer function is for the second sample port located at a distance of 15 cm in the classification region. The flow rates are 100:10 LPM. In determining the numerical transfer function effect of the other port has been neglected. The effect of the presence of the other port in upstream can be determined experimentally.

Figure 23:
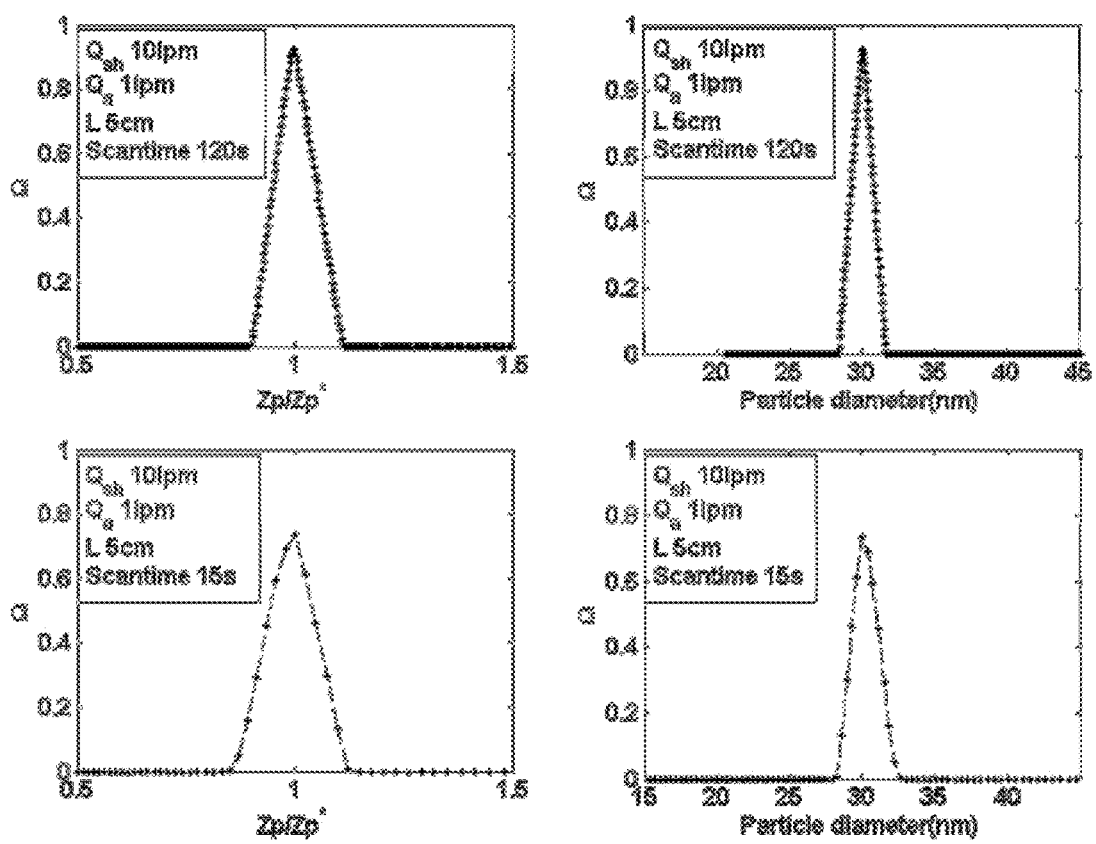
FIG. 23 also illustrates mobility-based and diameter based transfer function of the instrument.

FIG. 23 also illustrates the mobility-based and diameter based transfer functions of the instrument. Here the transfer function is for the first sample port located at a distance of 5 cm in the classification region.

Figure 24:
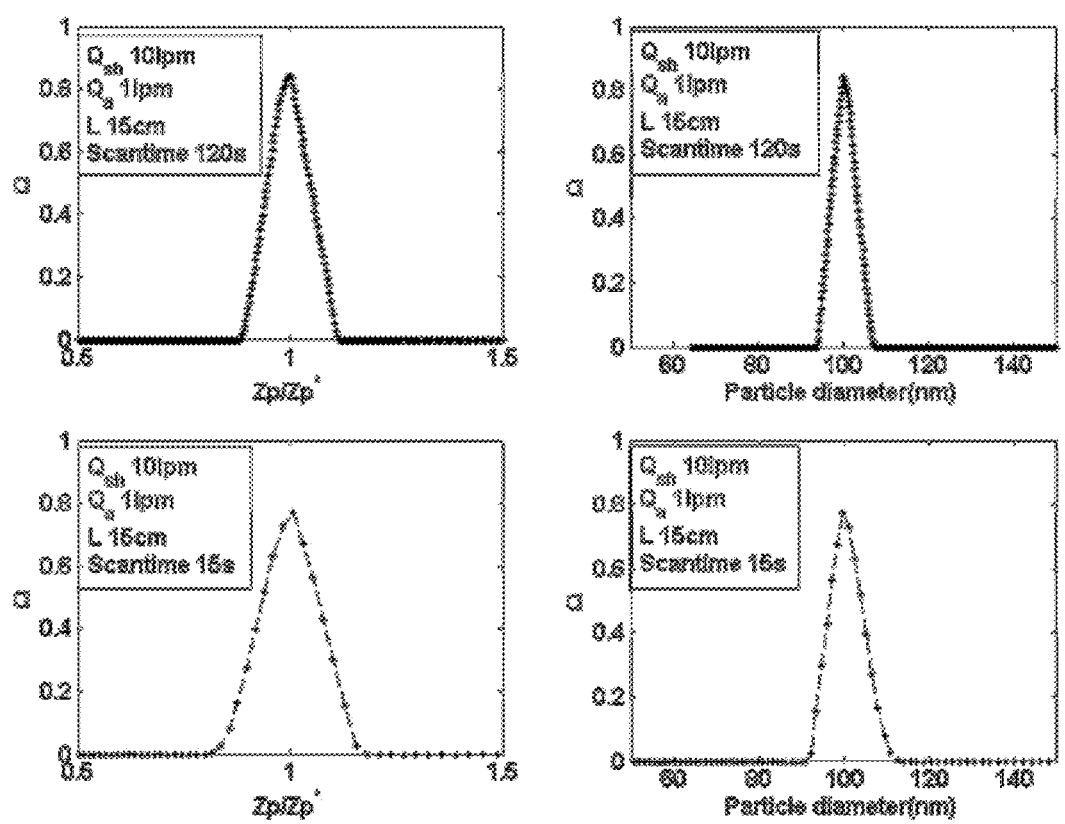
FIG. 24 also illustrates mobility based and diameter based transfer function of the instrument.

FIG. 24 also illustrates the mobility-based and diameter-based transfer function of the instrument. Here the transfer function is for the second port located at a distance of 15 cm in the classification region. The flow rates are 10:1 LPM. In determining the numerical transfer function effect of the other port has been neglected. The effect of the presence of the other port in upstream can be determined experimentally.

Figure 25:
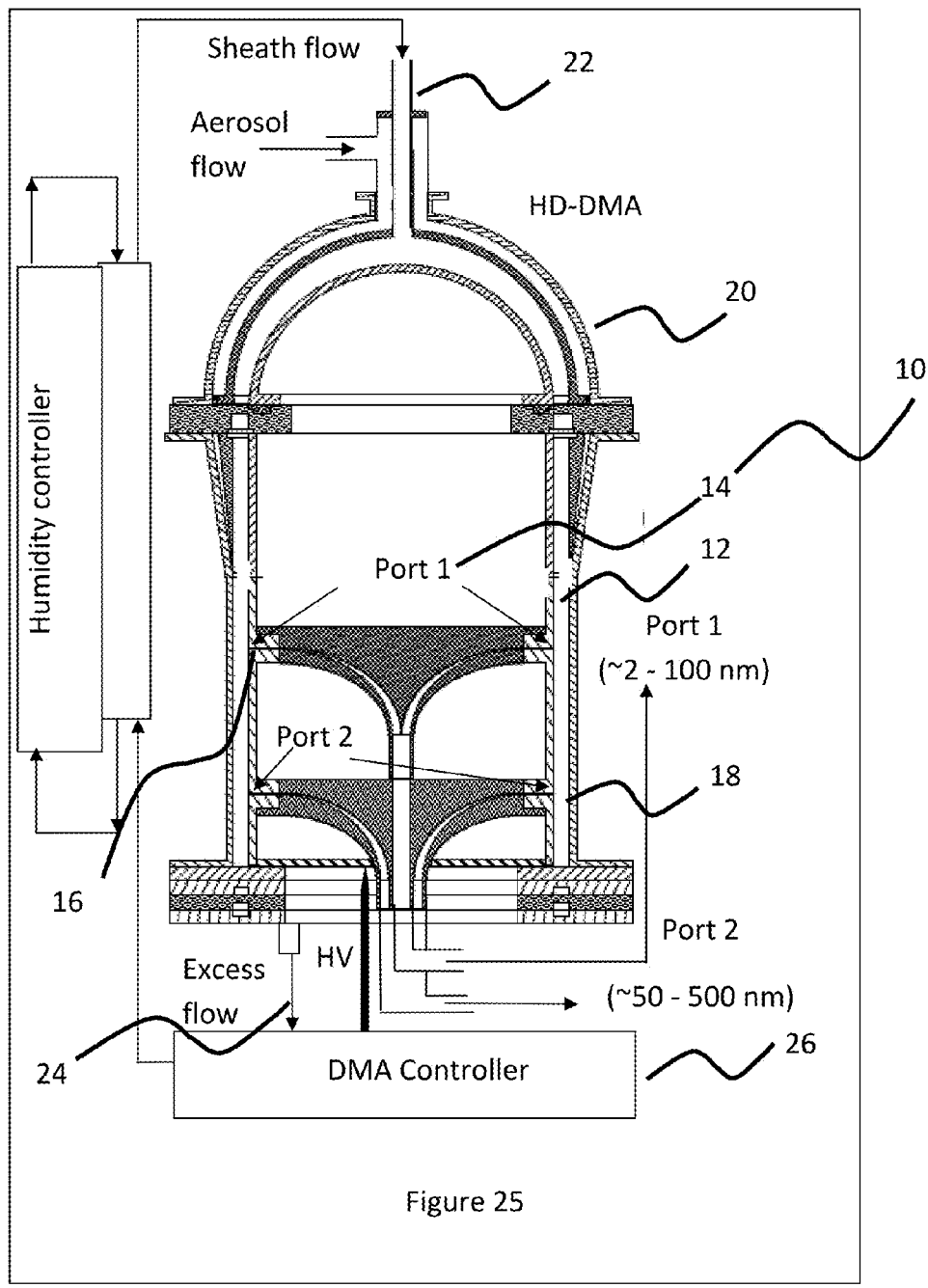
FIG. 25 illustrates a schematic diagram of the HD-DMA.

HD-DMA Design Details:

The schematic diagram of the HD-DMA 10 is shown in FIG. 25. To achieve the objectives of this instrument (high resolution, high flowrate), several new features are introduced. First, the annular region of the classification region 12 has a much greater radius while maintaining a narrow gap between the annular regions. The increase in the radius increases the area of the classification region and that helps increase the flow rate of the DMA operation, while maintaining a low Reynolds number. The HD-DMA permits a flow rate ~7 times greater than that in the commercially available DMA such as the TSI 3071 made by TSI Incorporated. The other advantage of greater radii of the annular classification region 14 is the small reduction in the residence time of particles in the classification region. This reduction in residence time increases the resolution of transfer function by reducing the diffusion effect of the particles (See Stolzenberg, 1988). The other major advantage of reduction in residence time is increase in the range of particle diameters classified during the scanning operation. Since particles have the finite residence-time in the classification region, the ratio of residence time to scan rate significantly affects the fast scanning operation (See above discussion and Dubey and Dhaniyala, 2008).

The second new feature of this instrument is the use of multiple sample ports 16 and 18. A preferred embodiment discussed below utilizes two ports. While there is on other design of DMA with multiple ports (Chen and Cheng 2007; Cheng and Chen—U.S. patent application Ser. No. 11/240,161, 2005) that design has sample ports on the outer cylinder, which makes sampling easier, but results in large recirculation regions in the sample ports and hence significant "smearing" of particle concentrations in the sample flow. That design would, therefore, not be applicable for fast size distribution measurements.

The sample ports designed here are concentric in the radii of the classification region from where the sample flow is collected symmetrically and can be used for further processing. The symmetrical collection of the sample flow removes any smearing problem that can be associated with the DMA during the scanning operation. The advantage of having multiport is that this increases the range of particles diameters that can be sampled from this instrument. The range of diameters sampled by each port has an overlap region. While the range of particle diameters sampled exclusively by one port increases the range of the DMA measurement, the range of particle diameter sampled by both the ports increases the information about the particle concentrations during the single scan. This implies that in a single scan this DMA can provide at least twice the information about certain particle diameters. This feature enables one to capture particle dynamics with greater accuracy. The combination of design improvement with the dual channel capability allows this instrument to sample wide range of particle diameter with greater sample flow (sample flow to sheath flow 1:10 LPM has range of 5 nm to 950 nm, 10:100 LPM has range of 1.7 nm to 170 nm; see FIG. 26). FIG. 26 illustrates the variation of sample particle size within sheath flow. The voltage range for operation is 10 to 10000V.

The HD-DMA is designed such that the polydisperse and sheath flows merge very smoothly avoiding flow disturbances near the junction. Also, a very gradual increase in outer radii of the classification region at the junction of the two flows is used to prevent undesirable electric field non-uniformity at the flow junction. The sample flows collected from the slit in the classification region, are gradually allowed to turn in the axial direction. Throughout the sample flow region, the flow is turned such that any undesirable flow recirculation is avoided and the Reynolds number in the sample flow region is always within the laminar flow regime (<2000).

At the entrance, hemispherical shapes 20 are used for gradual laminar, axisymmetric introduction of sheath and aerosol flows into the classification region. The relatively simple design of the clean sheath flow inlet 22 and the excess flow exit 24 makes it possible to circulate the excess flow to the sheath flow with an inline filter between the two ports. The low pressure drop design of the instrument permits the use of ordinary recirculatory blowers for the closed circuit flow between the sheath and excess ports. The integrated HD-DMA, and flow controller (fully computerized) setup is shown in FIG. 25.

The key dimensions of the HD-DMA include the following: Important dimension for HD-DMA: an inner radius of the classification region—10 cm; an outer radius of the classification region—11.02 cm; the length of port 1—5 cm; and the length of port 2—22.5 cm.

Within the DMA Controller 26, is a computer medium containing the software for executing the procedure used to calculate the arrival times and concentrations of particles at the exit of the classification region. In order to implement the method of calculating the arrival times and concentrations of particles at the exit of the classification region, a computer readable medium containing an executable program is used for calculating the arrival times and concentrations of particles at the exit of the classification region. This program includes: a first act of inputting an Initial value of $t_i$ and $r_i$, a second act of Estimating $t_b$ and $t_1$; a third act of Estimating $z_b$ and $z_1$; a fourth act of determining Is $z_b<L<z_1$?; a fifth act that if the determination in no, then Change the value $t_i$ or $r_i$ used as an initial value and if the determination is yes, Iterate between $t_1$ and $t_b$ to obtain $t_r$ with desired accuracy; and a sixth act of saving values of $r_i$, $t_i$ and $t_r$.

Experimental Results

Tandem DMA (TDMA) measurement was done with the upstream DMA as HD-DMA and downstream DMA as the TSI long or Nano DMA. Since the downstream DMA is calibrated, the inversion of TDMA measurements results gives the classified particle distribution downstream of HD-DMA. From these experiments, it was seen that the experimentally obtained peak mobilities matched well with the theoretical peak mobility for a given voltage (FIG. 4). The resolution of particle size distribution is seen to be approximately 75% of theoretical distribution (Stolzenberg 1988) (FIG. 5), consistent with the performance of other DMAs, e.g., the radial DMA.

Many variations and modifications may be made to the preferred embodiments of the disclosure as describe above. All such modifications and variations are intended to be herein within the scope of the present invention. It is therefore wished to have it understood that the present invention should not be limited in scope, except by the terms of the following claims.

REFERENCES

The following references are hereby incorporated by reference in full.

Agarwal, J. K. and Sem, G. J. (1980) Continuous flow, single-particle-counting condensation nucleus counter, J. Aerosol Sci. 11:343-357

Chen, D. and Pui, D. Y. H., (1997). Numerical modeling of the performance of differential mobility analyzers for nanometer aerosol measurements. J. Aerosol Sci. 28: 985-1004.

Collins, D. R., Cocker, D. R., Flagan, R. C., and Seinfeld, J. H. (2004) The Scanning DMA Transfer Function, Aerosol Science and technology. 38:833-850

Collins, D. R., Flagan, R. C., and Seinfeld, J. H. (2002) Improved Inversion of Scanning DMA Data, Aerosol Science and technology. 36:1-9

Ginsberg, E. S. and Zaborowski, D. (1975) The Dialogarithm Function of a real argument, Communication of the ACMs, 18:200-201.

Hagwood, C., Sivathanu, Y., and Mulholland, G. (1999). The DMA Transfer Function with Brownian Motion a Trajectory/Monte-Carlo Approach, Aerosol Sci. Technol. 30:40-61.

Han, H. S., Chen, D. R., Pui, D. Y. H., and Anderson, B. E. (2000). A Nanometer Aerosol Size Analyzer (ASA) for Rapid Measurement of High-Concentration Size Distributions, J. Nanoparticle Research 2:43-52.

Knutson, E. O., and Whitby, K. T. (1975). Aerosol classification by Electrical Mobility: apparatus theory and applications. J. Aerosol Sci. 6:443-451

Liu, N. Y. H., and Pui, D. Y. H. (1974). A submicron Aerosol Standard and the Primary, Absolute Calibration of the Condensation Nuclei Counter, J. Colloid and interface Sci. 47:155-171.

Russell, L. M., Flagan, R. C., and Seinfeld, J. H. (1995). Asymmetric Instrument Response Resulting from Mixing Effects in Accelerated DMA-CPC Measurements, Aerosol Sci. Technol. 23:491-509.

Shah, S. D. and Cocker, D. R. (2005). A Fast Scanning Mobility Particle Spectrometer for Monitoring Transient Particle Size Distributions, Aero. Sci. Technol. 39:519-526.

Stolzenburg, M. R. (1988). An Ultrafine Aerosol Size Distribution Measuring System, Ph.D. Thesis, University of Minnesota, Minneapolis Wang, S. C., and Flagan, R. C. (1990) Scanning Electrical Mobility Spectrometer, Aerosol Sci. Technol. 13: 230-240

We claim:

1. A differential mobility analyzer for aerosol measurements, comprising:
   a plurality of hemispheric entrance regions including at least one inlet for receiving an aerosol, said aerosol including a plurality of charged particles for analysis;
   a second at least one inlet separate from but concentric with said first inlet for receiving a sheath flow;
   a classifying region receiving said aerosol and sheath flow, said classifying region having an inner and outer radius and a plurality of parabolic shaped concentric output ports located in serially lower positions within said classifying region; and
   a source of voltage coupled to said inner and outer radius for creating an electric field within said classifying region.

2. The differential mobility analyzer of claim 1:
   wherein said inner radius and outer radius are large enough and a structure of said analyzer is such that there is a low Reynolds number of less than 2000, and hence laminar flow in said classifying region, while maintaining a sheath flow of up to 300 liters per minute.

3. The differential mobility analyzer of claim 2:
   wherein said inner radius is at least 10 cm.

4. The differential mobility analyzer of claim 2:
   wherein said outer radius is at least 11.02 cm.

5. The differential mobility analyzer of claim 2 wherein:
   said plurality of output ports includes a pair of output ports within said classifying region;
   an upper output port has a classification length of 5 cm and classifies particles within range of approximately 2 to 100 nm.; and
   a lower output port has a classification length of 22.5 cm and classifies particles within a range of approximately 50 to 500 nm.

6. The differential mobility analyzer of claim 2
   wherein a symmetric nature of a sheath flow entrance region permits said analyzer to operate down to very low flows of 3 LPM and up to flows in excess of 1000 LPM.

7. A method for measuring a size distribution of aerosols, comprising the steps of:
   providing a differential mobility analyzer;
   providing an aerosol including a plurality of charged particles for analysis;
   injecting said aerosol into a classifying region via a plurality of hemispheric entrance regions including at least one inlet for receiving said aerosol and a further providing a second at least one inlet separate from but concentric with said first inlet for receiving a sheath flow;
   coupling a voltage to an inner and an outer radius of said classifying region creating an electric field there between;
   providing a plurality of parabolic shaped concentric output ports located at a plurality of serially lower positions within said classifying region;
   withdrawing a sampling flow using said concentric output ports at at least two of said plurality of positions, wherein different mean particle sizes are withdrawn from respective ones of said concentric output ports.

8. The method for measuring a size distribution of aerosols of claim 7, wherein:
   a symmetric nature of a sheath flow entrance region permits said analyzer to operate down to very low flows of 3 LPM and up to flows in excess of 1000 LPM.

9. A differential mobility analyzer for aerosol measurements, comprising:
   a plurality of hemispheric entrance regions including at least one inlet for receiving an aerosol, said aerosol including a plurality of charged particles for analysis;
   a second at least one inlet separate from but concentric with said first inlet for receiving a sheath flow;
   a classifying region receiving said aerosol and sheath flow, said classifying region having an inner and outer radii and a plurality of parabolic or curved shaped concentric output ports located in serially lower positions within said classifying region;
   a source of voltage coupled to said inner and outer radius for creating an electric field within said classifying region, and wherein
   a plurality of said output ports open at a cylindrical wall of said classifying region.

10. The differential mobility analyzer of claim 9:
    further wherein a symmetric nature of said sheath flow inlet permits analyzer operation down to very low flows 3 LPM and has wide operational flow range 3-1000 LPM.

11. The differential mobility analyzer of claim 9 wherein:
    said analyzer uses a plurality of flows including:
    a polydisperse aerosol flow,
    a clean sheath flow,
    a plurality of monodisperse sample flows, and
    a residual excess flow; and
    wherein said polydisperse aerosol flow can be in a range of 0.3-100 LPM and
    further wherein said flow rate range of said plurality of monodisperse sample flows is the same as that of said polydisperse aerosol flow.

12. The differential mobility analyzer of claim 9, further comprising:
    a DMA controller that determines a transfer function of said analyzer that solves a trajectory equation to find a position of particles at different times in said classifying region; and
    determines a solution of said trajectory equation for a large number of particles injected at different locations.

13. The differential mobility analyzer of claim 9, further comprising:
    a DMA controller that calculates arrival times and concentrations of particles at an exit of said classifying region, the calculating including:
    inputting an initial value of an injection time ti and an initial value of a radial location at injection ri;
    estimating a time tb at a final radial location tb and a time t1 associated with a radial location at the inner radius of the classifying region;

estimating an axial location zb of a particle at time tb and an axial location z1 of a particle at time t1 for determining if zb<L<z1 when L is DMA classification length; wherein if said determination is no, then said DMA controller changes the value ti or ri used as an initial value; and wherein if said determination is yes, then said DMA controller iterates between t1 and tb to obtain an arrival time tr with desired accuracy, and saves values of ri, ti and tr.

* * * * *